(12) United States Patent
Rizk et al.

(10) Patent No.: US 10,500,303 B2
(45) Date of Patent: Dec. 10, 2019

(54) SELF-RETAINING SUTURES OF POLY-4-HYDROXYBUTYRATE AND COPOLYMERS THEREOF

(71) Applicant: Tepha, Inc., Lexington, MA (US)

(72) Inventors: Said Rizk, Windham, NH (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 795 days.

(21) Appl. No.: 14/821,145

(22) Filed: Aug. 7, 2015

(65) Prior Publication Data

US 2016/0045636 A1 Feb. 18, 2016

Related U.S. Application Data

(60) Provisional application No. 62/037,812, filed on Aug. 15, 2014.

(51) Int. Cl.
*A61L 17/10* (2006.01)
*A61B 17/06* (2006.01)
(Continued)

(52) U.S. Cl.
CPC ...... *A61L 17/105* (2013.01); *A61B 17/06166* (2013.01); *A61L 27/18* (2013.01);
(Continued)

(58) Field of Classification Search
CPC ........ A61L 17/105; A61L 17/12; A61L 31/06; A61L 27/18; C08L 67/04;
(Continued)

(56) References Cited

U.S. PATENT DOCUMENTS

| 3,598,122 A | 8/1971 | Zaffaroni |
| 3,598,123 A | 8/1971 | Zaffaroni |

(Continued)

FOREIGN PATENT DOCUMENTS

| CA | 2307637 | 5/1999 |
| CA | 2259098 | 7/1999 |

(Continued)

OTHER PUBLICATIONS

Agnew, et al., "Synthetic biology strategies for synthesizing polyhydroxyalkanoatesfrom unrelated carbon sources", Chem Eng Sci., 103:58-67 (2013).

(Continued)

*Primary Examiner* — Phong Son H Dang
(74) *Attorney, Agent, or Firm* — Pabst Patent Group LLP

(57) ABSTRACT

Absorbable monofilament fibers and self-retaining sutures with high tensile strengths have been developed. The straight pull tensile strengths of the absorbable self-retaining sutures closely approximate, equal or exceed the average minimum knot-pull tensile standards set by the United States Pharmacopeia (USP). These higher strength absorbable self-retaining sutures can therefore be used either without needing to oversize the suture for a given procedure, or by oversizing the self-retaining suture by no more than 0.1 mm in diameter. In one embodiment, the absorbable self-retaining sutures are made from poly-4-hydroxybutyrate or copolymers thereof.

Methods for producing absorbable self-retaining sutures that have high tensile strengths and pronounced sheath-core structures wherein the sheath is harder than the core are also provided. The self-retaining sutures may be made by spinning and orienting a monofilament fiber of poly-4-hydroxybutyrate or copolymer thereof and inserting retainers in monofilament fibers.

30 Claims, 6 Drawing Sheets

(51) Int. Cl.
*A61L 27/18* (2006.01)
*A61L 31/06* (2006.01)
*A61B 17/00* (2006.01)

(52) U.S. Cl.
CPC ..... *A61L 31/06* (2013.01); *A61B 2017/00004* (2013.01); *A61B 2017/00526* (2013.01); *A61B 2017/06176* (2013.01)

(58) Field of Classification Search
CPC .... A61B 17/06166; A61B 2017/00004; A61B 2017/06176; A61B 2017/00526
See application file for complete search history.

(56) References Cited

U.S. PATENT DOCUMENTS

| | | | |
|---|---|---|---|
| 3,731,683 A | 5/1973 | Zaffaroni | |
| 3,797,494 A | 3/1974 | Zaffaroni | |
| 3,982,543 A | 9/1976 | Schmitt | |
| 4,031,894 A | 6/1977 | Urquhart | |
| RE30,170 E | 12/1979 | Goodman | |
| 4,201,211 A | 5/1980 | Chandrasekaran | |
| 4,205,399 A | 6/1980 | Shataby | |
| 4,286,592 A | 8/1981 | Chandrasekaran | |
| 4,314,557 A | 2/1982 | Chandrasekaran | |
| 4,379,454 A | 4/1983 | Campbell | |
| 4,435,180 A | 3/1984 | Leeper | |
| 4,537,738 A | 8/1985 | Holmes | |
| 4,559,222 A | 12/1985 | Enscore | |
| 4,573,995 A | 3/1986 | Chen | |
| 4,588,580 A | 5/1986 | Gale | |
| 4,603,070 A | 7/1986 | Steel | |
| 4,645,502 A | 2/1987 | Gale | |
| 4,648,978 A | 3/1987 | Makinen | |
| 4,664,655 A | 5/1987 | Orentreich | |
| 4,704,282 A | 11/1987 | Campbell | |
| 4,711,241 A | 12/1987 | Lehmann | |
| 4,743,257 A | 5/1988 | Tormala | |
| 4,758,234 A | 7/1988 | Orentreich | |
| 4,788,062 A | 11/1988 | Gale | |
| 4,792,336 A | 12/1988 | Hlavacek | |
| 4,816,258 A | 3/1989 | Nedberge | |
| 4,826,493 A | 5/1989 | Martini | |
| 4,849,226 A | 7/1989 | Gale | |
| 4,853,226 A | 8/1989 | Machida | |
| 4,856,188 A | 8/1989 | Sibalis | |
| 4,876,331 A | 10/1989 | Doi | |
| 4,880,592 A | 11/1989 | Martini | |
| 4,908,027 A | 3/1990 | Enscore | |
| 4,910,145 A | 3/1990 | Holmes | |
| 4,938,763 A | 7/1990 | Dunn | |
| 4,943,435 A | 7/1990 | Baker | |
| 4,968,317 A | 11/1990 | Tormala | |
| 5,002,067 A | 3/1991 | Berthelsen | |
| 5,026,381 A | 6/1991 | Li | |
| 5,032,638 A * | 7/1991 | Wang | A61L 17/145 106/287.24 |
| 5,041,100 A | 8/1991 | Rowland | |
| 5,085,629 A | 2/1992 | Goldberg | |
| 5,124,371 A | 6/1992 | Tokiwa | |
| 5,128,144 A | 7/1992 | KorsatkoWabnegg | |
| 5,171,308 A | 12/1992 | Gallagher | |
| 5,204,382 A | 4/1993 | Wallace | |
| 5,222,976 A * | 6/1993 | Yoon | A61B 17/0469 606/223 |
| 5,236,431 A | 8/1993 | Gogolewski | |
| 5,245,023 A | 9/1993 | Peoples | |
| 5,250,430 A | 10/1993 | Peoples | |
| 5,271,961 A | 12/1993 | Mathiowitz | |
| 5,278,201 A | 1/1994 | Dunn | |
| 5,278,202 A | 1/1994 | Dunn | |
| 5,278,256 A | 1/1994 | Bellis | |
| 5,288,516 A | 2/1994 | Anderson | |
| 5,292,860 A | 3/1994 | Shiotani | |
| 5,306,286 A | 4/1994 | Stack | |
| 5,334,698 A | 8/1994 | Witholt | |
| 5,412,067 A | 5/1995 | Shinoda | |
| 5,443,458 A | 8/1995 | Eury | |
| 5,468,253 A | 11/1995 | Bezwada | |
| 5,480,394 A | 1/1996 | Ishikawa | |
| 5,480,794 A | 1/1996 | Peoples | |
| 5,489,470 A | 2/1996 | Noda | |
| 5,502,116 A | 3/1996 | Noda | |
| 5,502,158 A * | 3/1996 | Sinclair | A61L 15/26 528/354 |
| 5,512,669 A | 4/1996 | Peoples | |
| 5,516,565 A | 5/1996 | Matsumoto | |
| 5,516,883 A | 5/1996 | Hori | |
| 5,534,432 A | 7/1996 | Peoples | |
| 5,536,564 A | 7/1996 | Noda | |
| 5,550,173 A | 8/1996 | Hammond | |
| 5,551,954 A | 9/1996 | Buscemi | |
| 5,563,239 A | 10/1996 | Hubbs | |
| 5,584,885 A | 12/1996 | Becket | |
| 5,614,576 A | 3/1997 | Rutherford | |
| 5,625,030 A | 4/1997 | Williams | |
| 5,629,077 A | 5/1997 | Turnlund | |
| 5,635,215 A | 6/1997 | Boschetti | |
| 5,646,217 A | 7/1997 | Hammond | |
| 5,648,100 A | 7/1997 | Boschetti | |
| 5,670,161 A | 9/1997 | Healy | |
| 5,703,160 A | 12/1997 | Dehennua | |
| 5,705,187 A | 1/1998 | Unger | |
| 5,709,854 A | 1/1998 | GriffithsCima | |
| 5,711,933 A | 1/1998 | Bichon | |
| 5,728,752 A | 3/1998 | Scopelianos | |
| 5,735,863 A | 4/1998 | DellaValle | |
| 5,747,637 A * | 5/1998 | Shinoda | C08G 63/08 528/354 |
| 5,753,364 A | 5/1998 | Rutherford | |
| 5,753,708 A | 5/1998 | Koehler | |
| 5,789,536 A | 8/1998 | Liggat | |
| 5,811,272 A | 9/1998 | Snell | |
| 5,814,071 A | 9/1998 | McDevitt | |
| 5,814,599 A | 9/1998 | Mitragotri | |
| 5,824,333 A | 10/1998 | Scopelianos | |
| 5,824,751 A | 10/1998 | Hori | |
| 5,834,582 A | 11/1998 | Sinclair | |
| 5,840,331 A | 11/1998 | VanCauter | |
| 5,842,477 A | 12/1998 | Naughton | |
| 5,855,619 A | 1/1999 | Caplan | |
| 5,874,040 A | 2/1999 | Liggat | |
| 5,876,452 A | 3/1999 | Athanasiou | |
| 5,876,455 A | 3/1999 | Harwin | |
| 5,879,322 A | 3/1999 | Lattin | |
| 5,917,002 A | 6/1999 | Doi | |
| 5,919,478 A | 7/1999 | Landrau | |
| 5,935,506 A | 8/1999 | Schmitz | |
| 5,990,162 A | 11/1999 | Scharf | |
| 5,994,478 A | 11/1999 | Asrar | |
| 6,056,970 A | 5/2000 | Greenawalt | |
| 6,103,255 A | 8/2000 | Levene | |
| 6,119,567 A | 9/2000 | Schindler | |
| 6,162,537 A | 12/2000 | Martin | |
| 6,214,387 B1 | 4/2001 | Berde | |
| 6,245,537 B1 | 6/2001 | Williams | |
| 6,316,262 B1 | 11/2001 | Huisman | |
| 6,323,010 B1 | 11/2001 | Skraly | |
| 6,454,811 B1 | 9/2002 | Sherwood | |
| 6,514,515 B1 | 2/2003 | Williams | |
| 6,548,569 B1 | 4/2003 | Williams | |
| 6,555,123 B2 | 4/2003 | Williams | |
| 6,600,010 B2 | 7/2003 | Mao | |
| 6,610,764 B1 | 8/2003 | Martin | |
| 6,623,749 B2 | 9/2003 | Williams | |
| 6,645,622 B2 | 11/2003 | Yamane | |
| 6,656,489 B1 | 12/2003 | Mahmood | |
| 6,680,046 B1 | 1/2004 | Boschetti | |
| 6,770,356 B2 | 8/2004 | O'Donnell | |
| 6,838,492 B2 | 1/2005 | Williams | |
| 6,838,493 B2 | 1/2005 | Williams | |
| 6,848,152 B2 * | 2/2005 | Genova | A61B 17/06166 29/7.1 |
| 6,867,247 B2 | 3/2005 | Williams | |

(56) References Cited

U.S. PATENT DOCUMENTS

| | | | |
|---|---|---|---|
| 6,878,758 B2 | 4/2005 | Signer | |
| 7,070,610 B2* | 7/2006 | Im | A61B 17/06166 606/230 |
| 7,179,883 B2 | 2/2007 | Williams | |
| 7,244,442 B2 | 7/2007 | Williams | |
| 7,268,205 B2 | 9/2007 | Williams | |
| 7,553,923 B2 | 6/2009 | Williams | |
| 8,118,834 B1* | 2/2012 | Goraltchouk | A61B 17/06166 606/228 |
| 8,641,732 B1* | 2/2014 | Goraltchouk | A61B 17/06166 606/228 |
| 9,248,580 B2* | 2/2016 | Leung | B26D 3/08 |
| 9,775,928 B2* | 10/2017 | Ostapoff | A61L 17/105 |
| 10,280,532 B2* | 5/2019 | Simmelink | A61L 17/04 |
| 2002/0028243 A1 | 3/2002 | Masters | |
| 2002/0156150 A1 | 10/2002 | Williams | |
| 2002/0173558 A1 | 11/2002 | Williams | |
| 2003/0091803 A1 | 5/2003 | Bond | |
| 2003/0149447 A1* | 8/2003 | Morency | A61B 17/06166 606/228 |
| 2003/0185896 A1 | 10/2003 | Buiser | |
| 2003/0211131 A1 | 11/2003 | Martin | |
| 2004/0060409 A1* | 4/2004 | Leung | A61B 17/04 83/522.14 |
| 2004/0060410 A1* | 4/2004 | Leung | A61B 17/04 83/522.14 |
| 2004/0088003 A1* | 5/2004 | Leung | A61B 17/04 606/228 |
| 2004/0220355 A1 | 11/2004 | Whitehouse | |
| 2004/0234576 A1 | 11/2004 | Martin | |
| 2005/0107505 A1 | 5/2005 | Shinoda | |
| 2005/0267516 A1 | 12/2005 | Soleimani | |
| 2006/0058470 A1 | 3/2006 | Rizk | |
| 2007/0005110 A1* | 1/2007 | Collier | A61B 17/06166 606/228 |
| 2007/0016251 A1* | 1/2007 | Roby | A61L 17/04 606/228 |
| 2008/0027486 A1* | 1/2008 | Jones | A61B 17/0469 606/228 |
| 2008/0058869 A1* | 3/2008 | Stopek | A61B 17/06166 606/228 |
| 2008/0195147 A1* | 8/2008 | Stopek | A61L 17/005 606/228 |
| 2008/0281357 A1* | 11/2008 | Sung | A61B 17/06166 606/232 |
| 2008/0312688 A1* | 12/2008 | Nawrocki | A61B 17/06166 606/228 |
| 2009/0143819 A1* | 6/2009 | D'Agostino | A61L 17/12 606/228 |
| 2009/0182337 A1* | 7/2009 | Stopek | A61L 15/46 606/70 |
| 2009/0210006 A1* | 8/2009 | Cohen | A61B 17/06166 606/232 |
| 2010/0274282 A1* | 10/2010 | Olson | A61L 17/04 606/228 |
| 2010/0298872 A1* | 11/2010 | Berndt | A61B 17/06166 606/228 |
| 2011/0022086 A1* | 1/2011 | D'Agostino | A61L 17/08 606/231 |
| 2011/0046669 A1* | 2/2011 | Goraltchouk | A61B 17/06166 606/228 |
| 2011/0251639 A1* | 10/2011 | Thomas | A61B 17/06166 606/228 |
| 2012/0101522 A1* | 4/2012 | Megaro | A61B 17/06109 606/228 |
| 2012/0245629 A1* | 9/2012 | Gross | A61B 17/06166 606/228 |
| 2013/0172931 A1* | 7/2013 | Gross | A61F 5/566 606/230 |
| 2013/0238021 A1* | 9/2013 | Gross | A61B 17/06166 606/228 |
| 2013/0315963 A1* | 11/2013 | Erneta | C08L 67/04 424/400 |
| 2014/0277575 A1* | 9/2014 | Landgrebe | D01F 6/625 623/23.72 |
| 2014/0342109 A1* | 11/2014 | Mencke | D02G 3/02 428/36.3 |
| 2015/0272567 A1* | 10/2015 | Feezor | A61B 17/0485 606/232 |
| 2017/0156727 A1* | 6/2017 | Wilson-Wirth | A61L 17/105 |
| 2017/0189016 A1* | 7/2017 | Gross | A61B 17/06166 |
| 2017/0239383 A1* | 8/2017 | Koyfman | A61B 17/0401 |
| 2017/0281160 A1* | 10/2017 | Lin | A61B 17/06166 |
| 2017/0319203 A1* | 11/2017 | Cohen | A61B 17/06166 |

FOREIGN PATENT DOCUMENTS

| | | |
|---|---|---|
| CA | 2298421 | 2/2000 |
| DE | 3937649 | 5/1991 |
| EP | 0258781 | 3/1988 |
| EP | 0344704 | 12/1989 |
| EP | 0349505 | 3/1990 |
| EP | 0423484 | 4/1991 |
| EP | 0429403 | 5/1991 |
| EP | 0432443 | 6/1991 |
| EP | 0452111 | 10/1991 |
| EP | 0507554 | 10/1992 |
| EP | 0601885 | 6/1994 |
| EP | 0628586 | 12/1994 |
| EP | 0754467 | 1/1997 |
| EP | 0894505 | 2/1999 |
| EP | 1130043 | 9/2001 |
| EP | 1266984 | 12/2002 |
| GB | 2166354 | 5/1986 |
| JP | 62209144 | 9/1987 |
| JP | 03187386 | 8/1991 |
| JP | 04292619 | 10/1992 |
| JP | 04326932 | 11/1992 |
| JP | 05023189 | 2/1993 |
| JP | 05194141 | 11/1993 |
| JP | 06264306 | 9/1994 |
| JP | 06336523 | 12/1994 |
| JP | 07275344 | 10/1995 |
| JP | 08089264 | 4/1996 |
| JP | 0821216 | 8/1996 |
| JP | 08218216 | 8/1996 |
| JP | 09098793 | 4/1997 |
| JP | 09507091 | 7/1997 |
| JP | 2000220032 | 8/2000 |
| WO | 9218164 | 10/1992 |
| WO | 9305824 | 4/1993 |
| WO | 9320134 | 10/1993 |
| WO | 9402184 | 2/1994 |
| WO | 9406886 | 3/1994 |
| WO | 9503356 | 2/1995 |
| WO | 9517216 | 6/1995 |
| WO | 9520614 | 8/1995 |
| WO | 9520615 | 8/1995 |
| WO | 9520621 | 8/1995 |
| WO | 9523250 | 8/1995 |
| WO | 9533874 | 12/1995 |
| WO | 9600263 | 1/1996 |
| WO | 9608535 | 3/1996 |
| WO | 9618420 | 6/1996 |
| WO | 9621427 | 7/1996 |
| WO | 9640304 | 12/1996 |
| WO | 9704036 | 2/1997 |
| WO | 9707153 | 2/1997 |
| WO | 9715681 | 5/1997 |
| WO | 9730042 | 8/1997 |
| WO | 9804292 | 2/1998 |
| WO | 9839453 | 9/1998 |
| WO | 9848028 | 10/1998 |
| WO | 9851812 | 11/1998 |
| WO | 9911196 | 3/1999 |
| WO | 9914313 | 3/1999 |
| WO | 9932536 | 7/1999 |
| WO | 9935192 | 7/1999 |
| WO | 0051662 | 9/2000 |

(56) References Cited

FOREIGN PATENT DOCUMENTS

| WO | 0056376 | 9/2000 |
|---|---|---|
| WO | 0110421 | 2/2001 |
| WO | 0115671 | 3/2001 |
| WO | 0119361 | 3/2001 |
| WO | 02085983 | 10/2002 |
| WO | 03064531 | 8/2003 |
| WO | 101002 | 11/2004 |
| WO | 2012061658 | 5/2012 |

OTHER PUBLICATIONS

Anderson, et al., "Occurrence, Metabolism, metabolic Role, and Industrial Uses of bacterial Polyhydroxyalkanoates," Microbiological Reviews pp. 450-472 (1990).
Boeree, et al., "Development of a degradable composite for orthopaedic use: mechanical evaluation of an hydroxyapatite-polyhydroxybutyrate composite material", Biomaterials, 14 (10):793-6 (1993).
Braunegg, et al., "Polyhydroxyalkanoates, biopolyesters from renewable resources: physiological and engineering aspects," J. Biotech. 65: 127-161 (1998).
Breuer, et al., "Tissue Engineering Lamb Heart Valve Leaflets," Biotechnology & Bioengineering 50:562-67 (1996).
Campbell & Bailey, "Mechanical properties of suture materials in vitro and after in vivo implantation in horses," Vet. Surg. 21(5):355-61 (1992).
Clavijo-Alvarez, et al. "Comparison of biodegradable conduits within aged rat sciatic nerve defects," Plast Reconstr Surg. 119(6):1839-51(2007).
Gobert, et al., "Endotoxin: The uninvited guest", Biomaterials, 26:6811-7 (2005).
Gordeyev, et al., "Processing of gel-spun poly($^2$-hydroxybutyrate) fibers", Journal of Applied Polymer Science, 81:2260-2264 (2001).
Greenberg, "The Use of Barbed Sutures in Obstetrics and Gynecology", Rev Obstetrics Gynecology, 3(3):82-91 (2010).
Hazari, et al., "A new resorbable wrap-around implant as an alternative nerve repair technique", J. Hand Surgery, 24(3): 291-295 (1999).
Hazari, et al., "A resorbable nerve conduit as an alternative to nerve autograft in nerve gap repair", Br J Plast Surg., 52(8):653-7 (1999b).
Holmes, et al., "Applications of PHB a microbially produced biodegradable thermoplastic," Phys Technol 16:32-36 (1985).
Hori, et al., "Chemical synthesis of high molecular weight poly(3-hydroxybutyrate-co-4-hydroxybutyrate)" Polymer 36(24): 4703-4705 (1995).
Hori, et al., "Ring-Opening Copolymerization of Optically Active β-Butyrolactone with Several Lactones Catalyzed by Distannoxane Complexes: Synthesis of New Biodegradable Polyesters," Macromolecules 26:4388-90 (1993).
Ljungberg, et al. "Neuronal survival using a resorbable synthetic conduit as an alternative to primary nerve repair", Microsurgery, 19(6):259-264 (1999).
Malm, et al., "Enlargement of the right ventricular outflow tract and the pulmonary artery with a new biodegradable patch in transannular position," Eur. Surg. Res. 26(5):298-308 (1994).
Martin and Williams, "Medical application of poly-4-hydroxybutyrate: A strong flexible absorbable biomaterial", Biochem. Eng. J., 16:97-105 (2003).
Nakamura, et al., "Microbial synthesis and characterization of poly(3-hydroxybutyrate-co-4-hydroxybutyrate)," Macromol. 25:4237-41 (1992).
Niklason, et al., "Functional arteries grown in vitro," Science 284(5413):489-93 (1999).
Nobes, et al., "Polyhydroxyalkanoates: Materials for delivery systems," Drug Del. 5:167-77 (1998).
Odermatt, et al., "MonoMax Suture: A New Long-TermAbsorbableMonofilamentSutureMade from Poly-4-Hydroxybutyrate", J Polymer Sci., Article 216137 (2012).
Pinto, "Hydrogen Peroxide as depyrogenation agent for medical devices components", Revista De Saude Publica, 29(1):75-79 (1995).
Poirier, "Perspectives on the production of polyhydroxyalkanoates in plants," FEMS Microbiology Reviews 103:237-46 (1992).
Pouton & Akhtar, "Biosynthetic polyhydroxyalkanoates and their potential in drug delivery," Adv. Drug Delivery Rev. 18:133-62 (1996).
Rehm and Steinbuchel, "Biochemical and genetic analysis of PHA synthases and other proteins required for PHA synthesis", Int. J. Biol. Macromol. 25:3-19 (1999).
Renstad, et al., "The influence of processing induced differences in molecular structure on the biological and non-biological degradation of poly (3-hydroxybutyrate-co-3-hydroxyvalerate), P(3-HB-co-3-HV)," Polymer Degradation and Stability 63:201-211 (1999).
Rivard, et al., "Fibroblast seeding and culture in biodegradable porous substrates," J. Appl. Biomater. 6(1):65-68 (1995).
Ropero-Miller & Goldberger, "Recreational drugs. Current trends in the 90s", Clinics in Laboratory Medicine, 18:727-746 (1998).
Saito, et al., "Microbial synthesis and properties of poly(3-hydroxybutyrate-co-4-hydroxybutyrate) in Comamonas acidovorans," Int. J. Biol. Macromol. 16(2):99-104 (1994).
Schlosshauer, "Synthetic nerve guide implants in humans: a comprehensive survey." Neurosurgery 59:740-748 (2006).
Schmidt, et al "Neural tissue engineering: strategies for repair and regeneration," Annu. Rev. Biomed. Eng. 5:293-347 (2003).
Sendelbeck & Girdis, "Disposition of a 14C-labeled bioerodible polyorthoester and its hydrolysis products, 4-hydroxybutyrate and cis,trans-1,4-bis(hydroxymethyl)cyclohexane, in rats", Drug Metabolism & Disposition 13:291-295 (1985).
Shinoka, et al., "Creation of viable pulmonary artery autografts through tissue engineering," J. Thorac. Cardiovasc. Surg. 115(3):536-46 (1998).
Shinoka, et al., "Tissue engineering heart valves: valve leaflet replacement study in a lamb model" Ann. Thorac. Surg. 60(6 Suppl):S513-16 (1995).
Skrede et al, "Thia fatty acids, metabolism and metabolic effects" in Biochim Biophys Acta 1344:115-31 (1997).
Snead, "The gamma-hydroxybutyrate model of absence seizures: correlation of regional brain levels of gamma-hydroxybutyric acid and gamma-butyrolactone with spike wave discharges", Neuropharmacology 30:161-167 (1991).
Song, et al., "Production of poly(4-hydroxybutyric acid) by fed-batch cultures of recombinant strains of *Escherichia coli*", Biotechnol. Lett. 21:193-197 (1999).
Steinbüchel & Valentin, "Diversity of bacterial polyhydroxyalkanoic acids," FEMS Microbiol. Lett. 128:219-28 (1995).
Steinbüchel & Wiese, "A Pseudomonas strain accumulating polyesters of 3-hydroxybutyric acid and medium-chain-length 3-hydroxyalkanoic acids," Appl. Microbiol. Biotechnol. 37:691-97 (1992).
Steinbüchel, "Molecular basis for biosynthesis and accumulation of polyhydroxyalkanoic acids in bacteria," FEMS Microbiol. Rev. 103:217-230 (1992).
Takagi et al., "Biosynthesis of polyhydroxyalkanoate with a thiophenoxy side group obtained from Pseudomonas putida", Macromolecules, 32: 8315-8318 (1999).
Talja, et al., "Bioabsorbable and biodegradable stents in urology," J. Endourol. 11(6):391-97 (1997).
Tanahashi, et al., "Thermal Properties and Stereoregularity of Poly(3-hydroxybutyrate) Prepared from optically Active β-Butyrolactone with a Zinc-Based Catalyst," Macromolecules 24:5732-33 (1991).
Tanaka, et al., "Clinical application of 4-hydroxybutyrate sodium and 4-butyrolactone in neuropsychiatric patients", Folia Psychiatrica et Neurologica 20:9-17 (1966).
Tanguay, et al., "Current status of biodegradable stents," Cardiol. Clin. 12(4):699-713 (1994).
Tepha announces submission of device master file to FDA (Jun. 3, 2002), Retrieved Dec. 17, 2004, from http://www.pressrelease.be/script UK/newsdetail.asp?ndavs=m&ID=695.
Tepha submits device master file to FDA—New Technology (Jul. 2, 2002). Retrieved on Dec. 17, 2004, from http://www.findarticles.eom/p/articles/mi mOPC/is7 26/ai 89018276.
Türesin, et al., "Biodegradable polyhydroxyalkanoate implants for osteomyelitis therapy: in vitro antibiotic release," J. Biomater. Sci. Polymer Edn. 12: 195-207 (2001).

(56) References Cited

OTHER PUBLICATIONS

Turke, "Absorbable Biomaterial is suited for diverse applications" (Jun. 3, 2002). Retrieved on Dec. 17, 2004, from http://www.devicelink.com/mpmn/archive/01/10/009.html.

Unverdorben, et al., "Polyhydroxybutyrate (PHB) Biodegradable Stent-Experience in the Rabbit," American J. Cardiol. p. 46, TCT Abstracts (Oct. 1998).

Valappil, et al., "Biomedical applications of polyhydroxyalkanoates, an overview of animal testing and in vivo responses", Expert Rev. Med. Devices, 3(6):853-868 (2006).

Valentin, et al., "Identification of 5-hydroxyhexanoic acid, 4-hydroxyheptanoic acid and 4-hydroxyoctanoic acid as new constituents of bacterial polyhydroxyalkanoic acids," Appl. Microbiol. Biotechnol. 46:261-67 (1996).

Valentin, et al., "Production of poly(3-hydroxybutyrate-co-4-hydroxybutyrate) in recombinant *Escherichia coli* grown on glucose," J. Biotechnol. 58:33-38 (1997).

Von Schroeder, et al., "The use of polylactic acid matrix and periosteal grafts for the reconstruction of rabbit knee articular defects," J. Biomed. Mater. Res. 25(3):329-39 (1991).

Williams, et al., "PHA applications: addressing the price performance issue. I. Tissue engineering," Int. J. Biol. Macromol. 25(1-3): 111-121 (1999).

Williams, et al., "Poly-4-hydroxybutyrate (P4HB): a new generation of resorbable medical devices for tissue repair and regeneration", Biomed. Tech. 58(5):439-452 (2013).

Yamada, et al., "Development of a dural substitute from synthetic bioabsorbable polymers," J. Neurosurg. 86(6)1012-17 (1997).

Yiu, et al. "Glial inhibition of CNS axon regeneration," Nat. Rev. Neurosci. 7:617-627 (2006).

Zund, et al., "The in vitro construction of a tissue engineered bioprosthetic heart valve," Eur. J. Cardiothorac. Surg. 11(3):493-97 (1997).

\* cited by examiner

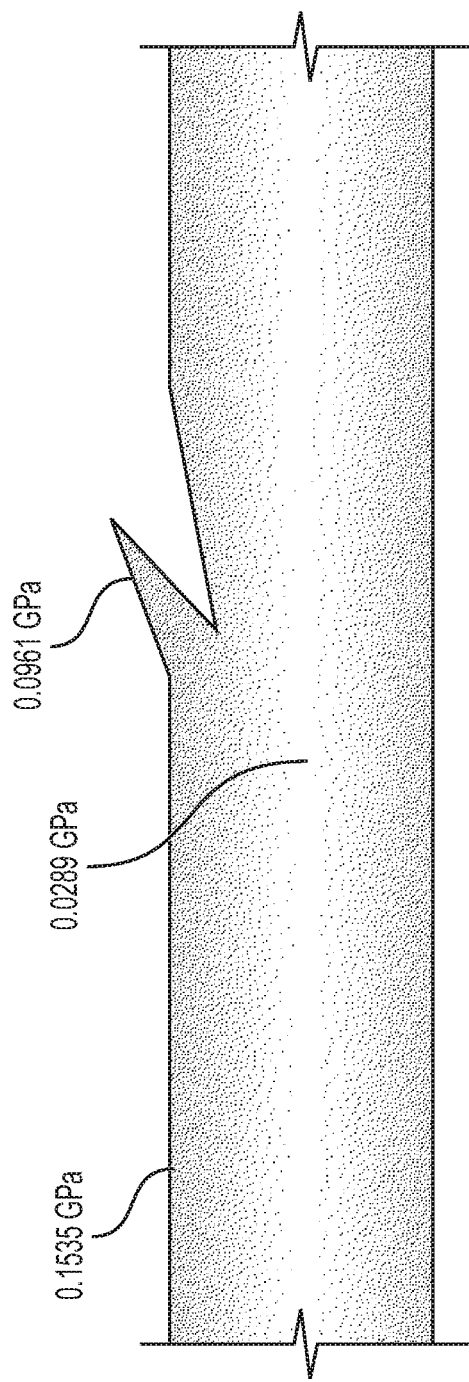

SELF-RETAINING SUTURES OF POLY-4-HYDROXYBUTYRATE AND COPOLYMERS THEREOF

CROSS REFERENCE TO RELATED APPLICATIONS

This application claims benefit of and priority to U.S. Provisional Patent Application No. 62/037,812 filed on Aug. 15, 2014, and is incorporated by reference in its entirety.

FIELD OF THE INVENTION

The present invention generally relates to self-retaining absorbable sutures of poly-4-hydroxybutyrate (P4HB) and copolymers thereof, with improved straight pull tensile strengths.

BACKGROUND OF THE INVENTION

Self-retaining sutures have previously been developed for use in wound closure, and other surgical procedures such as plastic surgery, see for example US Patent Application No. 2005/0267532 to Wu. These sutures contain tissue retainers (e.g. barbs) placed in a variety of different configurations along the suture fiber that when implanted project from the suture surface into tissue and resist movement in a direction opposite to the direction the tissue retainer faces.

The process of cutting tissue retainers into suture fiber decreases the cross-section of fiber that can support a load, and therefore cutting tissue retainers into a suture fiber decreases the straight pull tensile strength of the suture fiber. The straight pull tensile strength of a self-retaining suture is very important for several reasons. First, during implantation of the suture, force is applied along the axis of the suture fiber. The straight pull tensile strength of the self-retaining suture must be sufficient to prevent breakage of the suture during implantation. Second, immediately after placement, the suture must be strong enough to resist forces applied by the body, and particularly by strong muscles. For example, if the self-retaining suture is used in the face, the suture must be strong enough to resist forces applied by the patient when smiling, laughing, eating, frowning, etc. Third, if the self-retaining suture is absorbable it is vital that cutting tissue retainers in the suture does not decrease the strength retention profile so that it is too short to allow replacement of the suture's load carrying capacity by the body. For example, there should be enough time for the body to generate sufficient fibrotic tissue and adequate support before there is a critical loss of the suture's tensile strength (including the strength exerted by the tissue retainers).

Unfortunately, commercially available self-retaining absorbable sutures do not meet the US Pharmacopeia standard for average minimum knot-pull strength (measured by straight pull). For example, to meet the USP tensile strength for an absorbable suture of size 3-0, a surgeon must not only use a size 2-0 of Quill's Monoderm (a copolymer of glycolide and ε-caprolactone) self-retaining suture (see Angiotech product package insert P/N 03-5296R2), but the size 2-0 Quill Monoderm self-retaining suture also must have an oversized diameter. The size overage may be an increase in suture diameter of up to 0.1 mm. So, it is necessary not only to use a suture that is one size larger on the USP standards scale, but that is also oversized by up to 0.1 mm in diameter. Another example is Quill's PDO (polydioxanone) self-retaining sutures. To meet, for example, the USP tensile strength of a size 3-0 suture, a surgeon must not only use a size 2-0 of Quill's PDO (polydioxanone) self-retaining suture (see Angiotech product package insert P/N 03-5278R3), but also the size 2-0 suture must also be oversized in diameter by up to 0.1 mm. Greenberg, J. A. The use of barbed sutures in obstetrics and gynecology, *Rev. Obstet. Gynecol.* 3(3):82-91 (2010) also states clearly "Owing to its decreased effective diameter as a result of the process of creating barbs, barbed suture is typically rated equivalent to 1 USP suture size greater than its conventional equivalent. For example, a 2-0 barbed suture equals a 3-0 smooth suture". Consequently, surgeons are currently required to use suture diameters much larger than desired in order for the strength to be adequate for the repair, create suture tunnels in tissue that are larger than necessary, and in certain cases use sutures that are less pliable than might be desired.

Thus, in the practice of surgery there currently exists a need for absorbable self-retaining sutures with tensile strengths that meet or approximate (i.e. do not stray too far from) the standards of the US Pharmacopeia. These sutures would allow the surgeon to use smaller diameter sutures than is currently possible without compromising the tensile strength of the suture. The use of these absorbable self-retaining sutures would also decrease the amount of foreign material that needs to be implanted in the body, decrease the size of suture tunnels in a patient's tissues, and also provide more pliable suture options.

It is therefore an object of this invention to provide absorbable monofilament fibers and self-retaining sutures with high tensile strengths.

It is a further object of this invention to provide absorbable self-retaining sutures with smaller diameters and high tensile strengths.

It is yet a further object of this invention to provide absorbable self-retaining sutures with straight pull tensile strengths that equal or exceed the average minimum knot-pull tensile standards set by the United States Pharmacopeia (USP) wherein the self-retaining sutures are not oversized more than 0.1 mm in diameter.

It is still a further object of this invention to provide absorbable self-retaining sutures with high tensile strengths that are also pliable.

It is yet another object of this invention to provide methods to produce absorbable self-retaining sutures that have high tensile strengths.

It is still yet another object of this invention to provide methods to produce fibers of P4HB and copolymers thereof that have pronounced sheath-core structures wherein the sheath is harder than the core.

It is even yet another object of this invention to provide methods to implant absorbable self-retaining sutures that have high tensile strengths.

SUMMARY OF THE INVENTION

Absorbable monofilament fibers and self-retaining sutures with high tensile strengths have been developed. The straight pull tensile strengths of the absorbable self-retaining sutures closely approximate, equal or exceed the average minimum knot-pull tensile standards set by the United States Pharmacopeia (USP). In one embodiment, the sutures are made from poly-4-hydroxybutyrate or copolymers thereof.

The monofilament fibers of P4HB and copolymers have USP suture sizes ranging from size 4 to size 6-0 and Young's Modulus values that are preferably greater than 860 MPa, more preferably greater than 900 MPa, and even more preferably greater than 1 GPa. The diameters of the monofilament fibers of P4HB and copolymers may range from 0.05 mm to 1 mm, but are more preferably 0.07 mm to 0.799 mm, equivalent to USP suture size 6-0 to USP suture size 4 and oversized by up to 0.1 mm.

The straight pull tensile strengths of the monofilament fibers of P4HB and copolymers allow these fibers to be converted in some embodiments to self-retaining sutures with the following minimum straight pull tensile strengths: (i) 0.25 Kgf for a USP size 6-0 self-retaining suture; (ii) 0.68 Kgf for a USP size 5-0 self-retaining suture; (iii) 0.95 Kgf for a USP size 4-0 self-retaining suture; (iv) 1.77 Kgf for a USP size 3-0 self-retaining suture; (v) 2.68 Kgf for a USP size 2-0 self-retaining suture; (vi) 3.9 Kgf for a USP size 0 self-retaining suture; (vii) 5.08 Kgf for a USP size 1 self-retaining suture; (viii) 6.35 Kgf for a USP size 2 self-retaining suture; and (ix) 7.29 Kgf for a USP size 3 or 4 self-retaining suture.

Methods for producing monofilament fibers with high tensile strengths, hard surfaces and pronounced sheath-core structures are provided. In one preferred embodiment, these monofilaments are prepared by fiber spinning In a particularly preferred embodiment, the monofilament fibers used to make the high tensile strength self-retaining sutures are made by melt extrusion. The P4HB monofilament fibers may be prepared by: (i) drying bulk P4HB resin in pellet form until it has a water content of less than 300 ppm using a rotary vane vacuum pump system, (ii) transferring the dried pellets to the feed hopper of the extruder fitted with a dry nitrogen purge to keep the pellets dry, (iii) gravity feeding the P4HB pellets into a chilled feeder section, introducing the pellets into the extruder barrel, feeding the heated and softened resin into a heated metering pump (melt pump), and from the metering pump feeding the resin into a heated block and an eight-hole spinneret assembly, using a processing profile of 40° C. to 260° C. for temperatures, and 400 psi to 2,000 psi for pressures, (iv) water quenching the molten P4HB monofilaments, and (v) conveying the quenched filaments into a multi-stage orientation line, and stretching of at least 6×, before winding the high strength P4HB monofilament fiber on spools. Fibers with increased surface hardness values may be obtained by increasing the draw ratio during orientation of the fibers of P4HB and copolymers thereof. The draw ratio is preferably at least 6×, more preferably at least 6.5×, and even more preferably at least 7×. In a particularly preferred embodiment the draw ratio is 7.2× or more.

Methods for producing absorbable self-retaining sutures that have high tensile strengths and pronounced sheath-core structures wherein the sheath is harder than the core are also provided. The self-retaining sutures may be made by spinning and orienting a monofilament fiber of poly-4-hydroxybutyrate or copolymer thereof which has an average surface indentation hardness at least 0.07 GPa and inserting retainers in monofilament fibers. In one embodiment, the retainer-forming step includes cutting the high tensile strength absorbable monofilament fiber with a cutting element positioned at a desired angle relative to the longitudinal axis of the monofilament. In this embodiment, the angle of the cut forming the retainer measured relative to the longitudinal axis of the fiber is less than 90 degrees, more preferably less than 60 degrees, and even more preferably less than 45 degrees. In a preferred embodiment, the angle is between 15 and 45 degrees.

These higher strength absorbable self-retaining sutures can be used either without needing to oversize the suture for a given procedure, or by oversizing the self-retaining suture by no more than 0.1 mm in diameter. It is no longer always necessary to use an absorbable self-retaining suture that is one USP size larger than a conventional absorbable suture in order to meet the USP standard for initial tensile strength of a conventional absorbable suture. A surgeon may now use the same size of these high tensile strength self-retaining absorbable sutures as is conventionally used with non-barbed (smooth surface) absorbable sutures, or use a self-retaining absorbable suture that has only been oversized by less than 0.1 mm. The high tensile strength self-retaining absorbable sutures allow the surgeon to reduce the amount of foreign material that needs to be implanted in the patient's body, decreases the size of suture tunnels in a patient's tissues, and also provides more pliable sutures that can be easier to handle.

BRIEF DESCRIPTION OF THE DRAWINGS

FIG. 2 is a diagram of a high tensile strength self-retaining absorbable suture showing the difference in indentation hardness values between the difference in indentation hardness values between the surface (sheath) of a high strength P4HB monofilament fiber (0.1535 GPaand the indentation hardness of the core of the high strength P4HB self-retaining suture (0.0289 GPa)), and the indentation hardness of the retainers (0.0961 GPa)).

DETAILED DESCRIPTION OF THE INVENTION

I. Definitions

Figure 1:
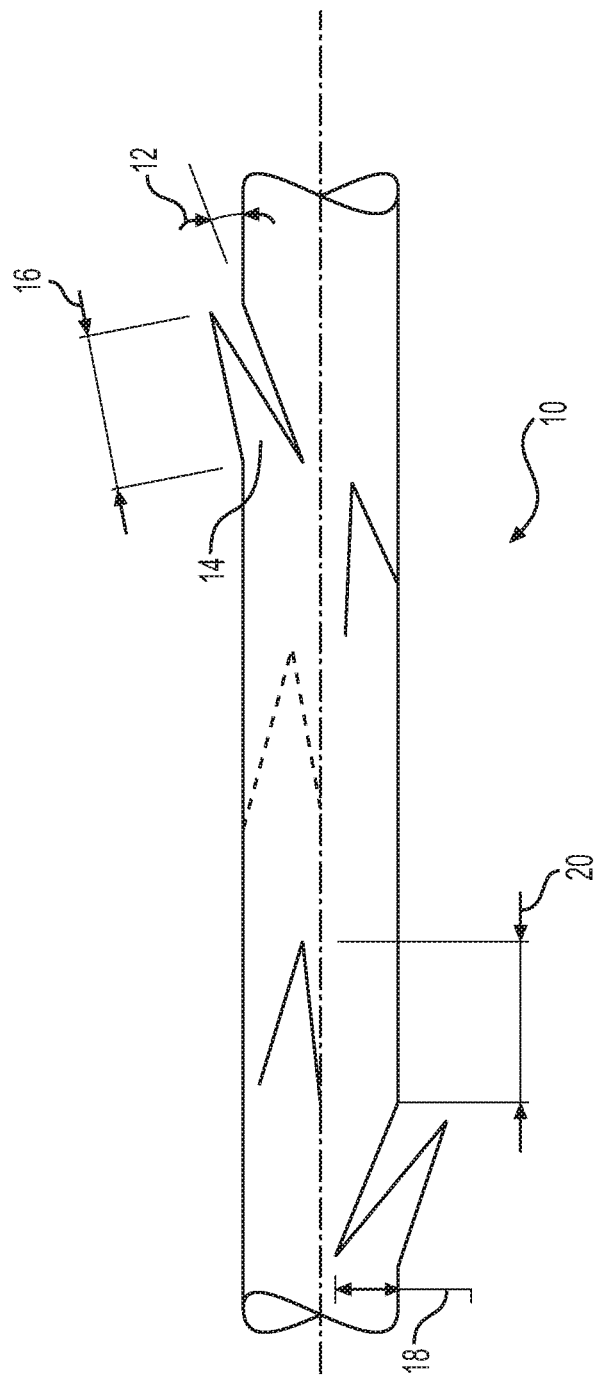
FIG. 1 is a diagram of a high tensile strength self-retaining absorbable suture (10) showing the cut depth (18), the cut spacing (spacing between the cuts) (20), the cut angle (the angle measured relative to the longitudinal axis of the monofilament fiber) (12), and the cut length (16).
Figure 2A:
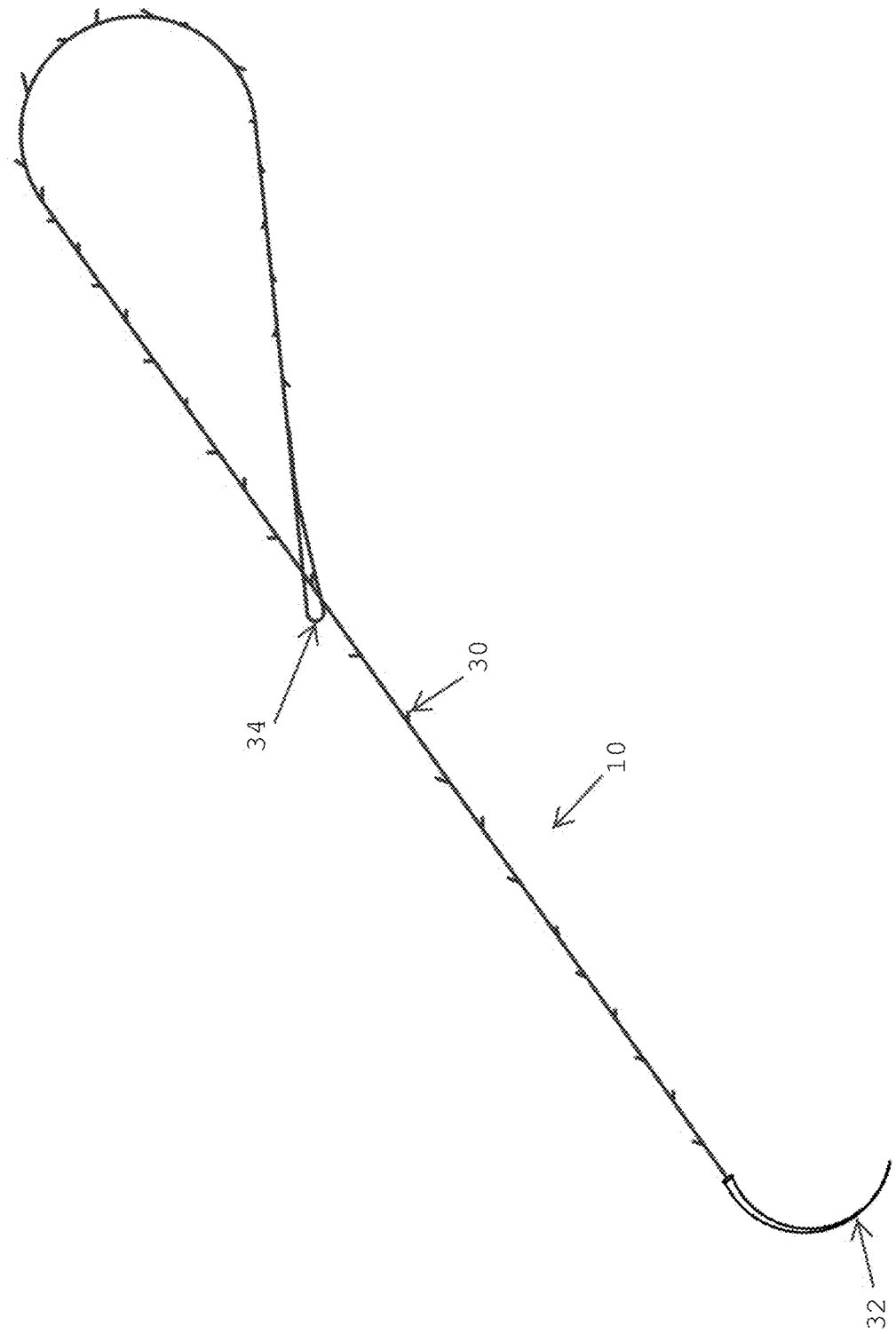
FIGS. 2A-2D show self-retraining sutures (10) with retainers (30), one (FIGS. 2A-C) or more (FIG. 2D) needles (32) and looped structure (34) (FIGS. 2B-C).
Figure 2B:
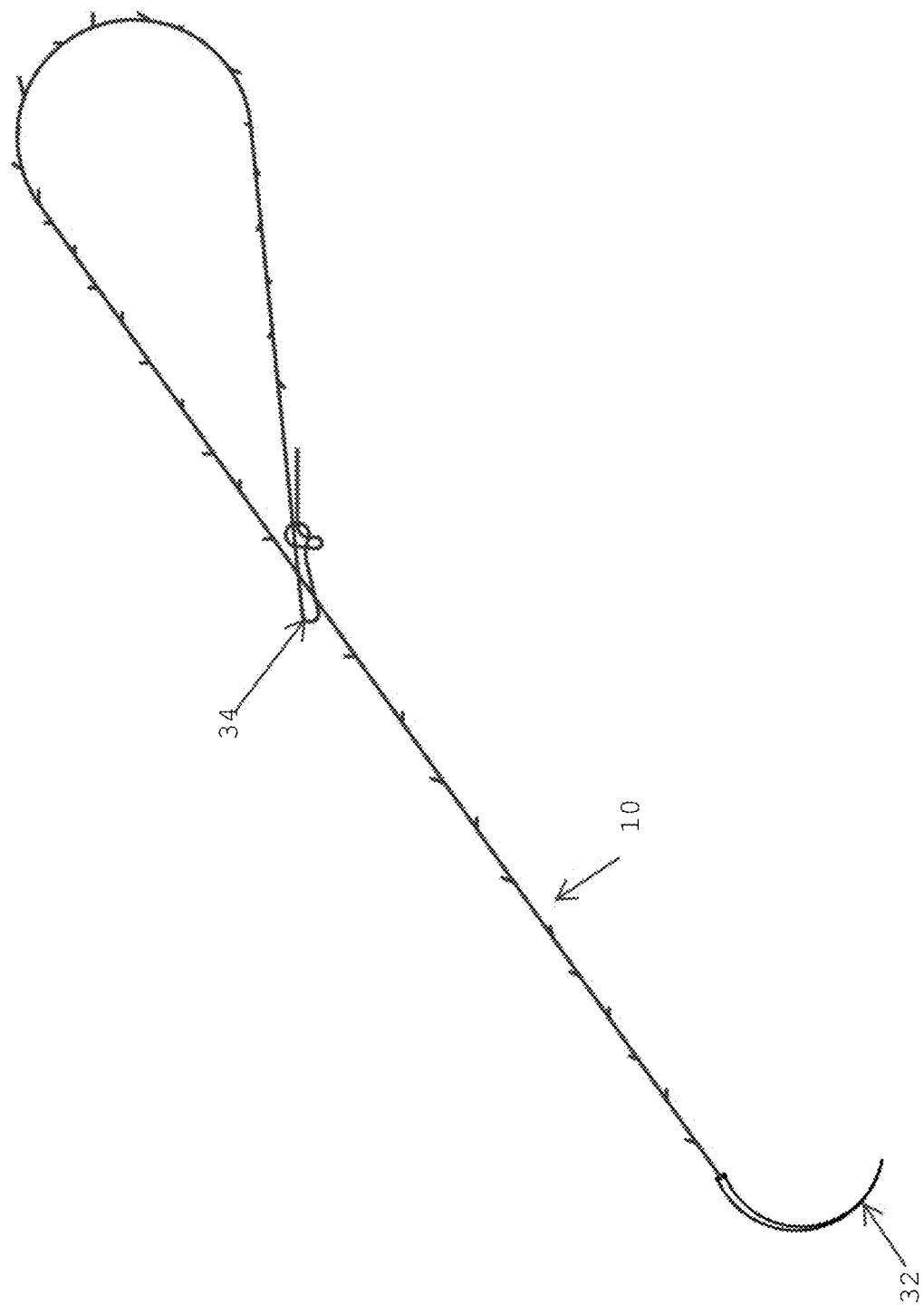
Figure 2C:
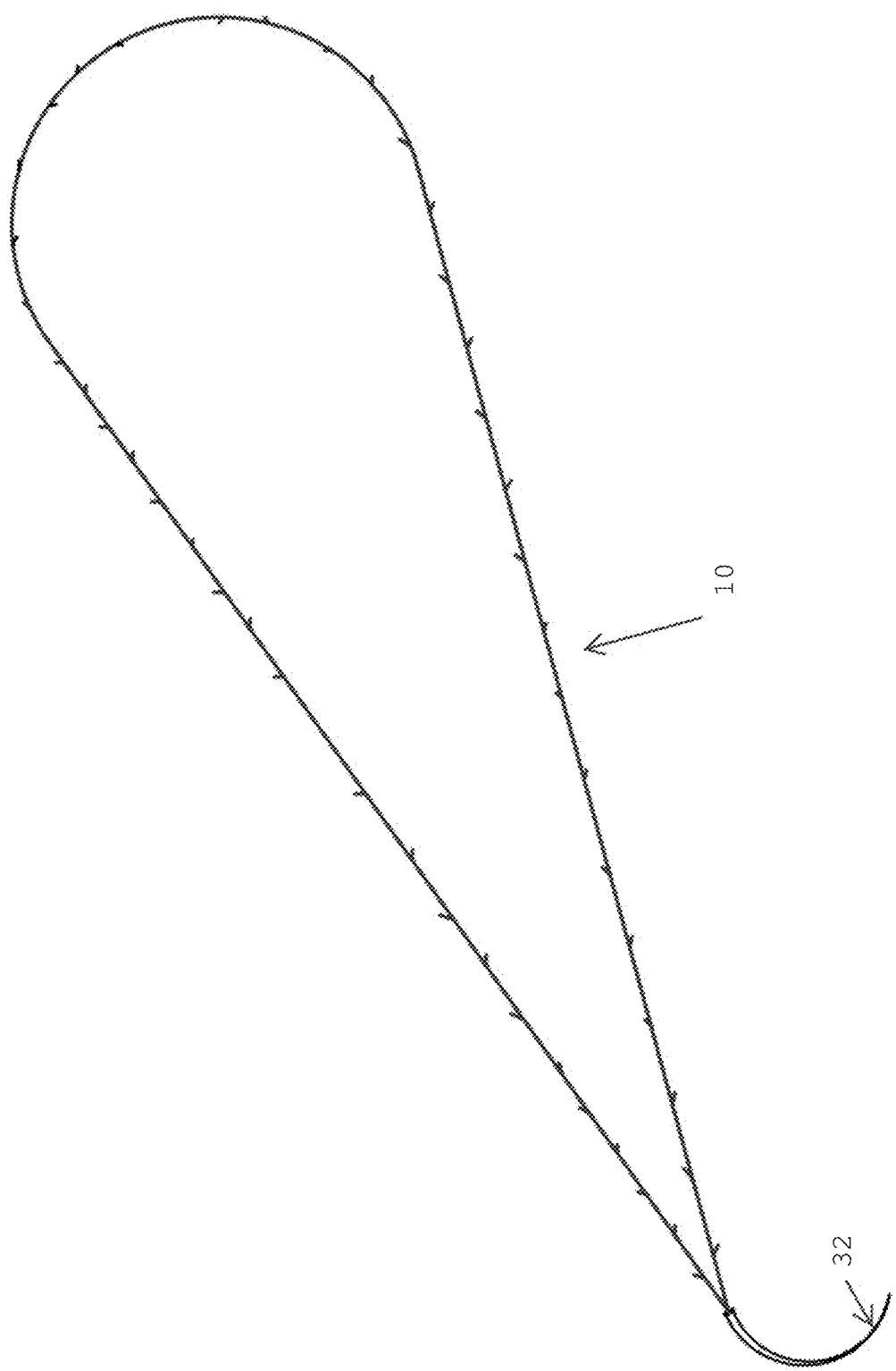
Figure 2D:
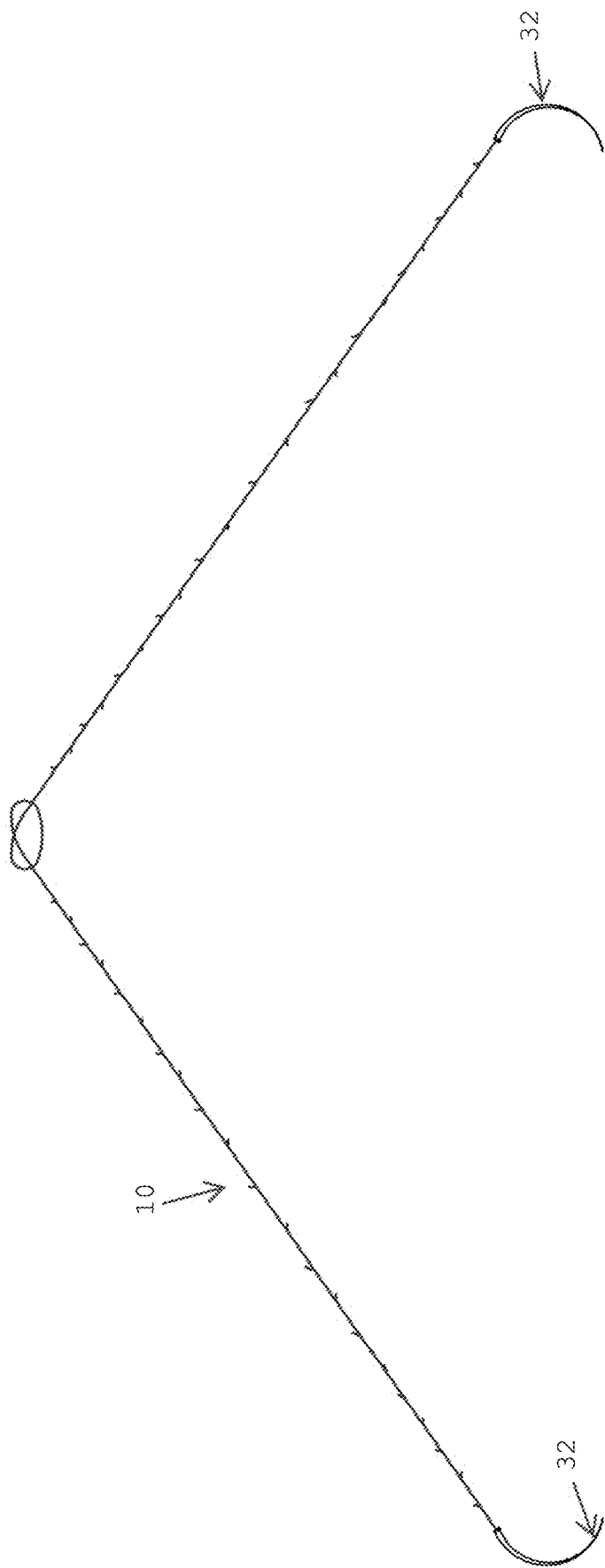

"Absorbable" as generally used herein means the material is broken down in the body and eventually eliminated from the body within five years.

"Bioactive agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of one or more symptoms of a disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, sugars, polysaccharides, nucleotides and, oligonucleotides, and combinations thereof.

"Bicomponent" as generally used herein means a monofilament structure made of two or more materials.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer comprised of two or more different monomers.

"Copolymers of poly-4-hydroxybutyrate" as generally used herein means any polymer of 4-hydroxybutyrate with one or more different hydroxy acid units.

"Diameter" as generally used herein is determined according to the US Pharmacopeia (USP) standard for diameter of surgical sutures (USP 861).

"Elongation to break" ("ETB") as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Indentation hardness" of fiber samples as used herein is determined by a nanoindentation technique at Polymer Solutions, Inc. (Blacksburg, Va.). Samples are embedded in epoxy and polished to give a flat surface on which to perform testing in accordance with PSI Method ID 6137 Revision 4. A diamond indenter is used to penetrate the sample with a force of 700 μN for 50 seconds, held for 10 seconds, and then retracted with 11 to 12 indentations made per sample. Hardness is calculated from the point at which the load reached a maximum using the equation H=Force (P)/Area (A), where H is hardness, P is the force and A is the area of the indent.

"Knot-pull tensile strength" as used herein is determined using a universal mechanical tester according to the procedures described in the US Pharmacopeia (USP) standard for testing tensile properties of surgical sutures (USP 881).

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer of 4-hydroxybutyrate units. It may be referred to herein as P4HB or TephaFLEX® biomaterial (manufactured by Tepha, Inc., Lexington, Mass.).

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Retainer" as generally used herein means a suture element that can project from the suture body, is adapted to penetrate tissue, and resist movement of the suture in any direction other than the direction in which the suture was deployed. Examples of retainers, include, but are not limited to, hooks, projections, barbs, darts, extensions, bulges, anchors, protuberances, spurs, bumps, points, cogs, tissue engagers, surface roughness, surface irregularities, surface defects, edges, and facets.

"Self-retaining suture" as generally used herein means a suture that contains one or more elements, or tissue retainers, to allow the suture to stay in position, and may not require a knot to maintain its position. In general, the tissue retainers project from the surface of the suture, and are designed to anchor in surrounding tissues. Sutures containing barbs projecting from the suture surface are examples of self-retaining sutures. Self-retaining sutures may be unidirectional, such that all the tissue retainers on the suture are oriented in the same direction, bidirectional such that some tissue retainers are oriented in one direction and others are oriented in another direction (which is generally in the opposite direction) or multidirectional.

"Sheath-core" as described herein refers to the cross-sectional structure of a fiber, wherein the properties of the sheath are different to the properties of the core, and the sheath and core cannot be physically separated. The term should not be confused with sheath-core structures wherein the sheath and core are two separate structures, for example, a multifilament sheath of fibers enclosing or covering a monofilament fiber core.

"Straight pull tensile strength" means the linear breaking strength of the specimen. The value may be determined using a tensile testing machine by holding the specimen between fixed and movable crossheads, and measuring the maximum tensile load per unit area of original cross section area of the specimen.

"USP Size" as used herein means the suture size prior to barbing or forming the self-retaining suture as defined by the United States Pharmacopeia. The USP Sizes can be 10, 9, 8, 7, 6, 5, 4, 3, 2, 1, 0, 2-0, 3-0, 4-0, 5-0, 6-0, 7-0, 8-0, 9-0, 10-0, 11-0 and 12-0.

II. Compositions

The compositions described herein are based on methods developed to produce absorbable self-retaining sutures containing P4HB and copolymers thereof with high straight pull tensile strength. The self-retaining sutures are made preferably from poly-4-hydroxybutyrate (P4HB) or a copolymer thereof. In some embodiments, the PHA polymers may be blended or mixed with other materials prior to preparing the self-retaining sutures. In addition to blending the P4HB polymers and copolymers with other polymers, additives may also be added to the polymers and copolymers prior to preparing fibers to manufacture self-retaining sutures.

A. Monofilament Fibers and Self-Retaining Sutures

Monofilament fibers of P4HB and copolymers thereof as well as self-retaining sutures of P4HB and copolymers thereof, are provided.

i) Monofilament Fibers

Oriented P4HB fibers with very hard surfaces that are ideally suited to making self-retaining sutures are provided. These monofilament fibers also have a high tensile strength and sheath-core structures.

Fibers of P4HB and copolymers thereof produced as described herein have a USP suture sizes ranging from size 4 to size 6-0 and Young's Modulus values that are preferably greater than 860 MPa, more preferably greater than 900 MPa, and even more preferably greater than 1 GPa. These values exceed those previously reported for monofilament fibers of P4HB and copolymers thereof by Martin, D. et al. Medical Applications of Poly-4-hydroxybutyrate: A Strong Flexible Absorbable Biomaterial, Biochem. Eng. J. 16:97-105 (2003), Williams, S. F. et al. Poly-4-hydroxybutyrate (P4HB): a new generation of resorbable medical devices for tissue repair and regeneration, Biomed. Tech. 58(5):439-452 (2013), and U.S. Pat. No. 7,641,825 to Rizk. Tables 3 and 4, for example, show the differences in Young's modulus values of representative high strength and medium strength P4HB monofilament fibers. Notably, the Young's modulus value for the high strength size 3-0 P4HB monofilament fiber is 1.8 GPa compared to just 0.79 GPa for the size 3-0 medium strength P4HB monofilament fiber. The higher stiffness, evident from both the higher Young's modulus and indentation hardness values, resulting from the pronounced sheath-core structure of the high strength fiber is important not only for ease of placing the retainers in the fiber, but also in producing retainers that will anchor in tissues and will not flex when a displacement force is applied.

The diameters of the monofilament fibers of P4HB and copolymers thereof may range from 0.05 mm to 1 mm, but are more preferably 0.07 mm to 0.799 mm, equivalent to USP suture size 6-0 to USP suture size 4 and oversized by up to 0.1 mm. In an embodiment, the diameters may be oversized relative to the USP standards by up to 0.1 mm. In a more preferred embodiment, the diameters of suture sizes 6-0 to 4-0 may be oversized by up to 0.05 mm, and the diameters of suture sizes 3-0 to 4 may be oversized by up to 0.1 mm.

(ii) Self Retaining Sutures

Self-retaining sutures with diameters ranging from approximately 0.07 mm to 0.8 mm with minimum tensile strength as listed in Table 1 (except measured by straight pull), and oversized by no more than 0.1 mm in diameter. The disclosed self-retaining sutures permit a surgeon to use smaller diameter self-retaining absorbable sutures than was previously possible.

The self-retaining sutures have certain properties, including: (i) ends that can penetrate tissue, (ii) the ability to lie flat when the suture is pulled in the deployment direction in order to generally avoid engaging with tissue, (iii) the ability to protrude from the suture surface and engage tissue when pulled in a direction opposite to the deployment direction so that tissue is engaged between the retainer and suture body so the suture is anchored in place, and (iv) sufficient stiffness or hardness to anchor in tissue, and hold the suture in place without the retainer flexing when a force is applied in a direction opposite to the deployment direction. The retainers may take many shapes, as. The retainers are preferably pointed or tapered at their free ends. The retainers may have a multi-tip configuration, in particular a twin-tip configuration such as a W-shaped formation. Retainers with a twin-tip configuration may be made using cuts into the monofilament fiber preferably with a small angular offset and in small intervals from each other.

The tissue retainers can be placed in a variety of different configurations along the suture fiber that when implanted project from the suture surface into tissue and resist movement in a direction opposite to the direction the tissue retainer faces. The tissue retainers may be unidirectional, such that the tissue retainers face in the same direction, or the tissue retainers may be oriented in a bidirectional manner along the suture surface. Orientation in a bidirectional manner means that a first group of at least one tissue retainer on a portion of the high strength suture is oriented in one direction while a second group of at least one tissue retainer is oriented in another direction, more preferably in an opposite direction.

The retainers may be positioned in an ordered or random manner, including spiral, staggered and overlapping configurations. In general, helical arrays of retainers are preferable because they hold the suture in place in tissue better than retainers placed along an axis. In addition, the distance between the retainers (i.e. retainer density), their angles, depths, and lengths (i.e. retainer geometries) may also be varied.

The retainers can be of various shapes, including, but not limited to, hooks, projections, barbs, darts, extensions, bulges, anchors, protuberances, spurs, bumps, points, cogs, tissue engagers, surface roughness, surface irregularities, surface defects, edges, facets, escutcheon-shaped, shield-shaped, scale-shaped, wedge-shaped, thorn-shaped, W-shaped, arrows, spikes, tin-shaped, V-shaped, and combinations thereof. The retainers are preferably pointed or tapered at their free ends. The retainers may have a multi-tip configuration, in particular a twin-tip configuration such as a W-shaped formation. In an embodiment, the distance between the retainers may be between 0 and 25 mm, but more preferably between 0 to 5 mm. Smaller distances between retainers are generally preferred in order to uniformly distribute tension along the suture line, and to provide more consistent wound approximation. In a preferred embodiment, the distance between retainers is preferably 0.5 to 2× the diameter of the suture.

If desired, the retainers may also be: (i) overlapped such that a retainer is cut into the fiber within the length of a prior retainer, (ii) positioned at the same distance along the fiber as another retainer, but in a different position on the circumference of the fiber, or (iii) positioned such that as one retainer ends another retainer starts either along the same axis or located somewhere else around the circumference of the fiber. In another embodiment, groups of retainers may be cut into the fibers, and larger spaces without retainers left between single retainers or groups of retainers.

In an embodiment, the length of the retainer may range from 0.25 to 2× the diameter of the suture, more preferably from 0.25 to 1.5× the diameter of the suture, and even more preferably equal 0.25 to 1.25× the diameter of the suture. Thus, the length of the retainer can be between 0.01-10 mm.

The straight pull tensile strengths of these absorbable self-retaining sutures exceed the average minimum knot-pull tensile strength standards set by the United States Pharmacopoeia (USP) with either no oversizing of the suture of at most oversizing of 0.1 mm or less.

The United States Pharmacopoeia (USP) defines sizes of absorbable sutures, and the average minimum knot-pull tensile strengths for a given absorbable suture size. The sizes, minimum and maximum average diameters, and average minimum knot-pull tensile strengths (in kgf) defined by the USP standard are shown in Table 1. Thus, for example, a size 5-0 suture must have a minimum average diameter of 0.1 mm, a maximum average diameter of 0.149 mm, and a minimum average knot-pull tensile strength of 0.68 kgf. It will be apparent by inspection of Table 1 that the knot-pull tensile strength of an absorbable suture increases as the diameter of the suture increases. The values shown in Table 1 are determined according to procedures defined in the US Pharmacopeia.

TABLE 1

Knot-Pull Tensile Strengths Defined by the USP Standards for Different Absorbable Suture Sizes

| USP Suture Size | Average Min. Diameter (mm) | Average Max. Diameter (mm) | Knot-Pull Tensile Strength (Average Min. kgf) |
|---|---|---|---|
| 10-0 | 0.020 | 0.029 | 0.025* |
| 9-0 | 0.030 | 0.039 | 0.050* |
| 8-0 | 0.040 | 0.049 | 0.07 |
| 7-0 | 0.050 | 0.069 | 0.14 |
| 6-0 | 0.070 | 0.099 | 0.25 |
| 5-0 | 0.10 | 0.149 | 0.68 |
| 4-0 | 0.15 | 0.199 | 0.95 |
| 3-0 | 0.20 | 0.249 | 1.77 |
| 2-0 | 0.30 | 0.339 | 2.68 |
| 0 | 0.35 | 0.399 | 3.90 |
| 1 | 0.40 | 0.499 | 5.08 |

TABLE 1-continued

Knot-Pull Tensile Strengths Defined by the USP Standards for Different Absorbable Suture Sizes

| USP Suture Size | Average Min. Diameter (mm) | Average Max. Diameter (mm) | Knot-Pull Tensile Strength (Average Min. kgf) |
|---|---|---|---|
| 2 | 0.50 | 0.599 | 6.35 |
| 3 and 4 | 0.60 | 0.699 | 7.29 |

*The tensile strength of these sizes is measured by straight pull

Notably, the US Pharmacopeia generally requires a manufacturer to report the knot-pull tensile strength of a suture rather than the straight-pull tensile strength because the former recognizes the reduction in strength that occurs when a suture is knotted. Self-retaining sutures are, however, an exception to this rule because self-retaining sutures are generally designed for use without a knot [see: Greenberg, J. A. *Rev. Obstet. Gynecol.* 3(3):82-91 (2010)]. Therefore, manufacturers report the tensile strengths of self-retaining sutures measured by straight pull, and compare these test values to the knot-pull tensile strength standards of the US Pharmacopeia. This approach makes sense since for a self-retaining suture its tissue holding capacity is most accurately reflected by its straight-pull tensile strength whereas the tissue holding capacity of a suture that needs to be knotted is most accurately reflected by its knot-pull tensile strength.

The standards for absorbable sutures set by the US Pharmacopeia are important to surgeons because they provide a standard system across all different types of absorbable suture sizes, regardless of material type, that allows the surgeon to select a specific suture size knowing that it will have sufficient initial mechanical properties (i.e. tensile strength) appropriate for an intended repair. For example, a surgeon selecting a size 3-0 absorbable suture expects the suture to have a minimum tensile strength of at least 1.77 Kgf, and that this strength is achieved within the set diameter range for a size 3-0 suture, namely from 0.20 to 0.249 mm. If however a suture does not meet the USP standard for tensile strength, it means that a surgeon may have to use a larger size of suture so that the suture has sufficient strength for the intended repair. In general, however, surgeons do not want to use larger sizes of suture than is absolutely necessary, and therefore it is important that sutures meet the USP standards or do not stray far from the standards. For example, a plastic surgeon undertaking a face-lift procedure will generally prefer to use sutures that meet or approximate the USP standard since the surgeon will not want to place larger sutures, and therefore more foreign material, in the patient's face in order to provide adequate tensile strength. The surgeons also generally prefer to keep the suture tunnel in the tissue as small as possible, and the pliability of the suture as high as possible so it is easy to implant. Both of these latter requirements are lost if the surgeon has to use a substantially larger diameter suture because the suture does not meet or approximate the USP standards for tensile strength.

A major advantage of the absorbable self-retaining sutures is that the sutures meet the requirements of the USP standards for knot pull strength (as measured by straight pull) or closely approximate the requirements of the USP standards. Notably, the absorbable self-retaining sutures do not need to be oversized by more than 0.1 mm in diameter to meet the USP standards, if at all. This means that a surgeon does not need to use an absorbable self-retaining suture that is both one size larger and oversized in order to have the tensile strength of a conventional suture. This reduces the amount of foreign material that needs to be implanted in a patient, and also reduces the size of suture tunnels made in the patient's tissues. Since the self-retaining sutures are absorbable, it also means that the time to complete degradation can, if desired, be faster in certain cases. Removing the requirement to use a self-retaining suture that is one size larger also means that the surgeon can work with a more pliable suture making implantation easier.

The high tensile strength absorbable self-retaining sutures of P4HB and copolymers thereof provided herein are biocompatible and can be used in soft and hard tissue repair, replacement, remodeling, and regeneration. Examples of applications for these high strength absorbable self-retaining sutures include wound closure, breast reconstruction and breast lift, including mastopexy procedures, lift procedures performed on the face such as face-lifts, neck lifts, and brow lifts, and ligament and tendon repair.

Self-retaining sutures can be made where all the tissue retainers face in the same direction, or different directions, for example, where the tissue retainers are oriented bi-directionally along the suture surface. The retainers may be positioned in an ordered or random manner, including spiral, staggered and overlapping configurations. In addition, the distance between the retainers, their angles, depths, and lengths may also be varied.

The straight pull tensile strengths of the monofilament fibers of P4HB and copolymers thereof produced by the processes described herein allow these fibers, with no more than a 0.1 mm variance in fiber diameter, to be converted to self-retaining sutures with the following minimum straight pull tensile strengths:

(i) 0.25 Kgf for a USP size 6-0 self-retaining suture; (ii) 0.68 Kgf for a USP size 5-0 self-retaining suture; (iii) 0.95 Kgf for a USP size 4-0 self-retaining suture; (iv) 1.77 Kgf for a USP size 3-0 self-retaining suture; (v) 2.68 Kgf for a USP size 2-0 self-retaining suture; (vi) 3.9 Kgf for a USP size 0 self-retaining suture; (vii) 5.08 Kgf for a USP size 1 self-retaining suture; (viii) 6.35 Kgf for a USP size 2 self-retaining suture; and (ix) 7.29 Kgf for a USP size 3 or 4 self-retaining suture. In an embodiment, the monofilament fibers of P4HB and copolymers thereof used to make the self-retaining sutures lose only 30-40% of their straight pull tensile strength when retainers are inserted in the fibers. In another embodiment, the monofilament fibers of P4HB and copolymers thereof used to make the self-retaining sutures have at least 2 times the straight pull tensile strength of the self-retaining sutures, and even more preferably at least 2.5 times the straight pull tensile strength of the self-retaining sutures.

Table 2 illustrates the difference in straight pull tensile strength of the self-retaining sutures made from high tensile strength monofilament fibers of P4HB compared to Quill's PDO absorbable self-retaining sutures (data taken from Angiotech product package insert P/N 03-5278R3) versus the USP standard. Both self-retaining sutures may be oversized by up to 0.1 mm, however, the Quill self-retaining sutures also need to be one size larger to meet the USP standard for tensile strength. In contrast, the high tensile strength P4HB self-retaining sutures do not need to be one size larger to meet the USP standard for tensile strength.

TABLE 2

Comparison of diameters of oversized Quill PDO and P4HB self-retaining sutures to the USP standard

| USP Suture Size | Tensile Strength (Average Min. Kgf) | Quill PDO Self-retaining suture, oversized by up to 0.1 mm | P4HB Self-retaining suture, oversized by up to 0.1 mm |
|---|---|---|---|
| 5-0 | 0.68 | 4-0 | 5-0 |
| 4-0 | 0.95 | 3-0 | 4-0 |
| 3-0 | 1.77 | 2-0 | 3-0 |
| 2-0 | 2.68 | 0 | 2-0 |
| 0 | 3.90 | 1 | 0 |
| 1 | 5.08 | 2 | 1 |

B. Polymers The high strength absorbable self-retaining sutures comprise poly-4-hydroxybutyrate (P4HB) or a copolymer thereof. Copolymers include 4-hydroxybutyrate copolymerized with another hydroxyacid, such as 3-hydroxybutyrate, and 4-hydroxybutyrate copolymerized with glycolic acid or lactic acid monomer.

Poly-4-hydroxybutyrate is not a natural product, and has never been isolated from a naturally occurring source. Poly-4-hydroxybutyrate (P4HB) can be produced, however, using transgenic fermentation methods, see, for example, U.S. Pat. No. 6,548,569 to Williams et al., and is produced commercially, for example, by Tepha, Inc. (Lexington, Mass.). Copolymers of poly-4-hydroxybutyrate can also be produced by transgenic fermentation methods, see also U.S. Pat. No. 6,548,569 to Williams et al.

Poly-4-hydroxybutyrate (P4HB, TephaFLEX® biomaterial) is a strong, pliable thermoplastic polyester that, despite its biosynthetic route, has a relatively simple structure. Upon implantation, P4HB hydrolyzes to its monomer, and the monomer is metabolized via the Krebs cycle to carbon dioxide and water.

Although man-made, P4HB belongs to a larger class of materials called polyhydroxyalkanoates (PHAs). PHA polymers include naturally occurring polymers produced by wildtype (naturally occurring) microorganisms, and PHA polymers that, like P4HB, are not naturally occurring [see, for example, Steinbüchel A., et al. Diversity of Bacterial Polyhydroxyalkanoic Acids, *FEMS Microbial. Lett.* 128:219-228 (1995) and Agnew D. E. and Pfleger, B. F. Synthetic biology strategies for synthesizing polyhydroxyalkanoates from unrelated carbon sources, Chemical Engineering Science 103:58-67 (2013)].

Chemical synthesis of P4HB has been attempted, but it has been impossible to produce the polymer with a sufficiently high molecular weight that is necessary for most applications, including melt processing [see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)]. In fact, it has been calculated to be thermodynamically impossible to chemically synthesize a high molecular weight homopolymer under normal conditions [Moore, T., et al., *Biomaterials* 26:3771-3782 (2005)]. Chemical synthesis of P4HB instead yields short chain oily oligomers that lack the desirable thermoplastic properties of the high molecular weight P4HB polymers produced by biosynthetic methods.

It should be noted that the literature commonly refers to another polyhydroxyalkanoate, poly-3-hydroxybutyrate (P3HB), simply as polyhydroxybutyrate (PHB) (see Section 2 of Moore, T., et al., *Biomaterials* 26:3771-3782 (2005)). Unlike P4HB, PHB is naturally occurring, and has entirely different properties to P4HB. PHB is structurally and functionally different to P4HB. For example, PHB has a melting point of 180° C. versus a melting point of about 61° C. for P4HB. The polymers also have substantially different glass transition temperatures and mechanical properties. For example, PHB is a relatively hard brittle polymer with an extension to break of just a few percent, whereas P4HB is a strong extensible polymer with an extension to break of about 1000%. As such, PHB has properties resembling polystyrene whereas P4HB has properties more similar to low density polypropylene. Not surprisingly, substantially different conditions are required to process these two polymers, and the resulting products have substantially different properties.

U.S. Pat. Nos. 6,245,537, 6,623,748, 7,244,442, and 8,231,889 describe methods of making PHA polymers with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III*, 4:91-127 (2002), Martin, D. et al., *Biochem. Eng. J.* 16:97-105 (2003), and by Williams, S. F. et al., *Biomed. Tech.* 58(5):439-452 (2013). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering.

U.S. Pat. No. 8,034,270 to Martin et al. discloses monofilament and multifilament knitted meshes of P4HB produced by knitting monofilament and multifilament fibers of P4HB. WO 2011/119742 to Martin et al. discloses P4HB monofilament and multifilament fiber, coatings and spin finishes for these fibers, and medical devices made from P4HB monofilament and multifilament fibers. U.S. Pat. No. 8,016,883 to Coleman et al. discloses methods and devices for rotator cuff repair, including medical devices containing knitted meshes of P4HB and nonwovens made from P4HB multifilament fibers.

U.S. Pat. No. 8,287,909 to Martin et al. discloses medical devices containing melt-blown nonwovens of poly-4-hydroxybutyrate and copolymers thereof with average fiber diameters of 1 μm to 50 μm. WO 2011/159784 to Cahil et al. discloses medical devices containing dry spun nonwovens of P4HB and copolymers thereof, and continuous processing methods for their preparation.

Odermatt et al., *Int. J. Polymer Science*, Article 216137, 12 pages (2012) and U.S. Pat. Nos. 7,641,825 and 8,084,125 to Rizk disclose non-curling sutures of P4HB. Odermatt et al. and Rizk do not disclose high strength absorbable self-retaining P4HB sutures. Instead they disclose P4HB suture fiber that has not been highly oriented, and has been relaxed to reduce the curling of the suture fiber. Relaxing the suture fiber decreases the tensile strength of the fiber. For example, the tensile strength of the relaxed size 3/0 suture fiber reported by Rizk is 4.148 Kgf, compared to 6.9 Kgf.

US Patent Application No. 2010/0057123 to D'Agostino and Rizk, and US Patent Application No. 2009/0112259 to D'Agostino disclose recombinant expressed bioabsorbable polyhydroxyalkanoate monofilament and multi-filament self-retaining sutures. There is no disclosure of the straight pull tensile strength of the self-retaining sutures, and no disclosure of how to produce self-retaining PHA sutures with high tensile strength. The applications do disclose the extensions to break ranging from 8% to 42% for the self-retaining sutures, however, it should be noted that the applications do not disclose the extensions to break of the PHA monofilament fibers used to make the self-retaining sutures. In fact, the applications do not disclose any details regarding the properties of PHA monofilament fibers that are necessary to make self-retaining sutures. There is absolutely no disclosure of how to make PHA self-retaining sutures that have straight pull tensile strengths that approximate, equal or exceed the average minimum knot-pull tensile strength standards set by the United States Pharmacopeia (USP). There is no disclosure recognizing the potential to produce, or need to produce, self-retaining sutures that approximate or meet the requirements of the USP standards for both diameter and tensile strength, nor any disclosure of the problems that can be overcome by producing such high strength self-retaining sutures that approximate or meet the USP standards for absorbable sutures. There is also no disclosure of the problems that need to be overcome in order to manufacture a PHA self-retaining suture with a tensile strength that approximates, equals or exceeds the average knot-pull tensile strength standard set by the USP.

US Patent Application No. 2012/0053689 to Martin et al. discloses barbed sutures made from polyhydroxyalkanoate polymers, including devices comprising a monofilament core with an outer multifilament sheath (such that the barbed monofilament core anchors the outer multifilament sheath). Martin et al. do not disclose self-retaining sutures with high straight pull tensile strength, or self-retaining sutures with such strength that approximates, equals or exceeds the average minimum knot-pull tensile strength standards set by the USP. In fact, there is no disclosure recognizing the potential to produce, how to produce, or need to produce, self-retaining sutures that approximate or meet the requirements of the USP standards for both diameter and tensile strength.

In a preferred embodiment, the P4HB homopolymer and copolymers thereof used to prepare the high tensile strength self-retaining sutures have a weight average molecular weight, Mw, within the range of 50 kDa to 1,200 kDa (by GPC relative to polystyrene) and more preferably from 100 kDa to 600 kDa.

If desired, the PHA polymers may be blended or mixed with other materials prior to preparing the self-retaining sutures. In a preferred embodiment, P4HB and its copolymers may be blended with other absorbable polymers. Examples of other absorbable polymers include, but are not limited to, polymers containing glycolic acid, lactic acid, 1,4-dioxanone, trimethylene carbonate, 3-hydroxybutyric acid, and ε-caprolactone, and include polyglycolic acid, polyglycolide, polylactic acid, polylactide, polydioxanone, polycaprolactone, copolymers of glycolic and lactic acids such as VICRYL® polymer, and the MAXON® and MONOCRYL® polymers. If desired, the P4HB homopolymer and copolymers thereof may also be blended with natural absorbable polymers, such as collagen, silk, proteins, polysaccharides, glycosaminoglycans, hyaluronic acid, heparin, and chitosan, as well as other components prior to preparing PHA fibers suitable for making the self-retaining sutures. The ratio of the PHA polymer in the blend to the non-PHA polymer component(s) may be varied in order to select the desired properties of the self-retaining suture. However, the ratio of the non-PHA to the PHA polymer should not be so high that it causes the resulting self-retaining suture to have a straight pull tensile strength less than, or approximate to, the average minimum knot-pull tensile strength standard set by the United States Pharmacopoeia (USP). This also applies to copolymers of P4HB. The ratio of co-monomers in a P4HB copolymer should not be so high that it causes the self-retaining suture to have a straight pull tensile strength less than, or approximate to, the average minimum knot-pull tensile strength standard set by the United States Pharmacopoeia (USP). In an embodiment, a self-retaining suture made from a P4HB copolymer or blend of P4HB with another material meet the USP standard except the suture may be oversized by up to 0.1 mm in diameter.

C. Additives

In addition to blending the P4HB polymers and copolymers with other polymers, additives may also be added to the polymers and copolymers prior to preparing fibers to manufacture self-retaining sutures. Preferably, these additives are incorporated during the compounding process to produce pellets that can be subsequently processed into fibers suitable for making high strength self-retaining sutures. In another embodiment, the additives may be incorporated using a solution-based process. In a preferred embodiment, the additives are biocompatible, and even more preferably the additives are both biocompatible and absorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the P4HB homopolymer, copolymer or blend. Such agents may be used to improve the mechanical properties of fibers, and to reduce cycle times. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl ricinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

Other additives that can be incorporated into the P4HB polymer and copolymers thereof include, but are not limited to, compatibilizers, porogens, dyes, and organic or inorganic powders including fillers and bioceramics. Particularly preferred bioceramics are degradable, and include tricalcium phosphate (α and β forms of TCP—with a nominal composition of $Ca_3(PO_4)_2$), biphasic calcium phosphate (BCP), calcium sulfate, calcium carbonate, hydroxyapatite and other calcium phosphate salt-based bioceramics. Bio-active glasses may also be incorporated prior to preparing fibers suitable for making high tensile strength self-retaining sutures.

It may also be advantageous to incorporate contrast agents, radiopaque markers, imaging agents, or radioactive substances into the P4HB polymer and copolymers thereof prior to spinning fibers suitable for making high tensile strength self-retaining sutures. Alternatively, these can be incorporated into or onto the high tensile strength self-retaining sutures during subsequent processing steps.

The self-retaining sutures may also be coated with materials to further improve their performance. For example, the self-retaining sutures may be coated to improve their lubricity. Coatings that can be applied to increase the lubricity of the self-retaining sutures include wax, natural and synthetic polymers such as polyvinyl alcohol, and spin finishes including TWEEN® 20, and polymers or oligomers of ethylene oxide and propylene oxide. These coatings are preferably applied so the self-retaining suture to a coating weight of less than 6 wt %, and more preferably less than 3 wt %. It is preferred that the coatings readily leave the surface of the self-retaining suture in vivo, for example, by degradation or dissolution, for example, being formed of a water-soluble material which dissolves.

D. Bioactive Agents

In an embodiment, bioactive agents may be incorporated into the P4HB polymer or copolymer thereof. Bioactive agents may be incorporated either prior to spinning fibers suitable for making high tensile strength self-retaining sutures, for example, during blending or pelletization, or alternatively, these agents may be incorporated into or onto the high tensile strength self-retaining sutures during subsequent processing steps. In one embodiment, the bioactive agents, and the P4HB polymer or copolymer thereof, may be dissolved in a solvent or solvent system in order to disperse the bioactive agent in the P4HB polymer or copolymer thereof, and the solvent may then be removed by evaporation. Preferred solvents include methylene chloride, chloroform, tetrahydrofura, acetone, dimethylformamide, and 1,4-dioxane.

Examples of bioactive agents that can be incorporated into the P4HB polymer, copolymer, or blends thereof, include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, and signaling ligands. These may be synthetic or nature materials such as platelet rich plasma, peptides, proteins, glycoproteins, sugars, polysaccharides, lipids, lipoproteins, nucleotides and oligonucleotides such as antisense molecules, aptamers, and siRNA, inorganics such as hydroxyapatite and silver particles, or small molecules. Examples include anesthetics, hormones, antibodies, growth factors, fibronectin, laminin, vitronectin, integrins, antibiotics, steroids, vitamins, non-steroidal anti-inflammatory drugs, chitosan and derivatives thereof, alginate and derivatives thereof, collagen, hyaluronic acid and derivatives thereof, allograft material, xenograft material, ceramics, and combinations thereof.

III. Methods of Manufacturing High Strength Self-Retaining Sutures of P4HB and Copolymers Thereof A. Methods of Manufacturing Fibers Methods are provided for manufacturing monofilament fibers of P4HB and copolymers thereof with high tensile strength, sheath-core structures, and high surface hardness, as well as self-retaining sutures of P4HB and copolymers thereof.

In a preferred embodiment, these monofilaments are prepared by fiber spinning.

In a particularly preferred embodiment, the monofilament fibers used to make the high tensile strength self-retaining sutures are made by melt extrusion. In one embodiment, P4HB monofilament fibers may be prepared using an American Kuhne melt extruder with a 1.5 inch extruder barrel, fitted with an extrusion screw with a 30:1 L/D ratio, and containing 5 heating zones, by (i) drying bulk P4HB resin in pellet form until it has a water content of less than 300 ppm using a rotary vane vacuum pump system, (ii) transferring the dried pellets to the feed hopper of the extruder fitted with a dry nitrogen purge to keep the pellets dry, (iii) gravity feeding the P4HB pellets into a chilled feeder section, introducing the pellets into the extruder barrel, feeding the heated and softened resin into a heated metering pump (melt pump), and from the metering pump feeding the resin into a heated block and an eight-hole spinneret assembly (using a processing profile of 40° C. to 260° C. for temperatures, and 400 psi to 2,000 psi for pressures) (iv) water quenching the molten P4HB monofilaments, and (v) conveying the quenched filaments into a multi-stage orientation line, and stretching of at least 6×, before winding the high strength P4HB monofilament fiber on spools.

As well as providing high tensile strength fibers of P4HB and copolymers thereof, the procedure described above also produces P4HB fibers with very hard surfaces that are ideally suited to making self-retaining sutures. Moreover, it has been discovered that oriented fibers of P4HB and copolymers thereof can be produced with well-defined sheath-core structures in which the sheath has a highly oriented crystalline structure while the core, although still semi-crystalline, has less orientation than the sheath. The differences in orientation and crystallinity between the sheath and the core mean that the fiber has a hard surface and a softer inner core.

Adjustment of the monofilament fiber orientation process allows the hardness of the fiber surface to be regulated, and permits the production of high strength self-retaining sutures of P4HB and copolymers thereof. Thus, monofilament fibers with increased surface hardness values may be obtained by increasing the draw ratio during orientation of the fibers of P4HB and copolymers thereof. The draw ratio is preferably at least 6×, more preferably at least 6.5×, and even more preferably at least 7×. In a particularly preferred embodiment the draw ratio is 7.2× or more. Importantly, unlike prior disclosures such as U.S. Pat. Nos. 7,641,825 and 8,084,125 to Rizk, the monofilament fiber is not significantly relaxed in a separate step after orientation. For example, the oriented monofilament fiber is not stretched 7×, and then allowed to relax to a draw ratio of 6.5× as shown in Comparative Example 1. Relaxation results in a significant decrease in tensile strength of the fiber, and a significant decrease in surface hardness. Table 3 shows the difference in indentation hardness values between the surface (sheath) and core of high strength P4HB monofilament fibers, and the difference in indentation hardness values between the surface of a high strength P4HB self-retaining suture, the core of a high strength P4HB self-retaining suture, and the surface of a medium strength P4HB monofilament fiber. Several conclusions may be drawn from Table 3. First, it is clear that for the medium strength P4HB monofilament fiber, the indentation hardness of the surface (0.0473) is significantly less than that of the high strength P4HB monofilament fiber (0.1535 GPa). And second, the indentation hardness of the retainers of the high strength P4HB self-retaining suture (0.0961 GPa) is much higher than the indentation hardness of the core of the high strength P4HB self-retaining suture (0.0289 GPa).

TABLE 3

Indentation hardness (GPa) comparing indentation hardness of P4HB monofilament fiber samples

| Sample | Indentation Hardness (GPa) |
|---|---|
| Medium strength P4HB monofilament fiber, size 2, 55% ETB, SURFACE | 0.0473 |
| High strength P4HB monofilament fiber, size 2, 25% ETB, SURFACE | 0.1535 |
| High strength P4HB self-retaining suture, size 2, 25% ETB, CORE | 0.0289 |
| High strength P4HB self-retaining suture, size 2, 25% ETB, SURFACE (RETAINER) | 0.0961 |

The hardness of a fiber's surface is an important property in the preparation of self-retaining sutures. For example, if the surface is too soft, it will be difficult to cut retainers in the fiber surface. This is because the surface of a soft suture fiber will plastically deform when a cutting machine applies pressure. The deformation of the fiber surface may either prevent the fiber from being cut, or result in a sub-optimal cut. Not only will it be difficult to cut the surface of the fiber if the fiber surface is too soft, but the retainers cut in the suture will not be hard enough to anchor in tissue, and will flex and not be retained in the tissue when a force is applied. Consequently, the discovery that unoriented P4HB fibers with very soft surfaces (e.g. tensile modulus of 70 MPa) can be oriented to provide fibers with sheath-core structures containing very hard surfaces is important in the production of high tensile strength P4HB self-retaining sutures and their ability to anchor securely in a patient's tissues.

B. Introduction of Retainers in High Tensile Strength Absorbable Monofilament Fibers In an embodiment, the absorbable self-retaining sutures are made by inserting retainers in the high tensile strength absorbable monofilament fibers of P4HB and copolymers thereof.

Referring to the self-retaining suture (10) shown in FIG. 1, in one embodiment, the angle (12) of the cut forming the retainer (14) measured relative to the longitudinal axis of the suture fiber (10) is less than 90 degrees, more preferably less than 60 degrees, and even more preferably less than 45 degrees. In a preferred embodiment, the angle (12) is between 15 and 45 degrees. The angle (12) and cut length (16) determine the depth (18) of the cut.

Retainers may be cut into the high tensile strength absorbable monofilament fiber (20) to any depth (18) provided the cuts are not so deep that it causes the resulting self-retaining suture to have a straight pull tensile strength less than the average minimum knot-pull tensile strength standard set by the United States Pharmacopoeia (USP). The exact depth of the cuts in the monofilament fiber will depend on the diameter of the self-retaining suture that is being produced. Typically, the depths (18) of cuts in the monofilament fibers, measured perpendicular from the monofilament surface, will be in the range of 1.0 to 300 μm, depending upon the diameter of the self-retaining suture that is being produced. In an embodiment, the depth of retainers cut into the high strength absorbable monofilament fiber may be up to 40% or more of the diameter of the monofilament fiber.

In an embodiment, the retainer-forming step includes cutting the high tensile strength absorbable monofilament fiber with a cutting element positioned at a desired angle relative to the longitudinal axis of the monofilament (see angle shown in FIG. 1). The cutting element is controlled such that it makes the cut not only at a desired angle (12), but also for a desired length (16) and depth (18). Additional retainers may be cut in the fiber at any desired distance from each other (20), and also, if desired, placed around the circumference of the fiber (for example, to make a helical pattern). The angles, lengths and depths of the retainers cut in the fiber may also be varied.

The cuts in the fiber may be made by any suitable method, including simply using a cutting blade or more preferably micromachining equipment designed to cut retainers of various shapes, lengths, and depths into the fiber at different angles and also, if desired, placing the retainers around the circumference of the fiber. In another embodiment, the retainers may be cut using a laser. In a particularly preferred embodiment, micromachining is used to manufacture the self-retaining sutures from the high tensile strength monofilament fibers. Methods for placing retainers in monofilament fibers are known in the art, and can be used to place retainers in the monofilament fibers of P4HB and copolymers thereof. For example, a method of making a self-retaining suture by varying the blade geometry and/or the movement of the blade when cutting a fiber is described in U.S. Pat. No. 6,848,152. A station for forming barbs in a suture is disclosed in U.S. Patent Application No. 2010 0275750. U.S. Pat. No. 8,032,996 discloses an apparatus for forming barbs on a suture. The apparatus has a filament supply and an in-feed collet for holding one end of a filament threaded there through. Further the apparatus has an out-feed collet for holding a second end of a filament threaded there through. The apparatus also has a holder positioned between the in-feed and out-feed collets for holding a filament suspended between the in-feed and out-feed collets. The apparatus also has a cutting assembly for cutting barbs in the filament tensioned between the in-feed and out-feed collets.

C. Incorporation of Bioactive Agents in High Tensile Strength Absorbable Self-Retaining Sutures Bioactive agents may be incorporated into the high tensile strength absorbable self-retaining sutures either prior to spinning of the high strength monofilament fiber, prior to inserting retainers in the monofilament fiber, or after retainers have been inserted in the monofilament fiber. In the former case, the bioactive agents may be blended with poly-4-hydroxybutyrate and copolymers thereof prior to spinning. Alternatively, the bioactive agents may be applied to the monofilament fiber before or after inserting retainers. In one embodiment, the bioactive agents may be dissolved to form a solution or suspended in a solution, and applied to the fiber. Solutions and suspensions may be applied to the fiber by spray coating, dip-coating, immersion, painting, electrostatic spraying, pad printing, wiping, and brushing. In a preferred embodiment, the bioactive agents are dissolved in non-solvents for poly-4-hydroxybutyrate and copolymers thereof so that the bioactive agents may be applied to the fiber without solubilizing the fiber or softening the fiber surface. After application of the bioactive agents, non-volatile solvents, such as water, may be removed by vacuum drying. This is particularly important to protect the suture from hydrolysis, and loss of polymer molecular weight. Solvents that may be used to coat the fibers with bioactive agents include, but are not limited to, water, alcohols including methanol, ethanol and isopropanol, ether, hexane and other non-polar organic solvents.

D. Structures Containing Self-Retaining High Tensile Strength Absorbable Sutures The high tensile strength self-retaining absorbable sutures may be used in suturing applications with or without needles. Needles may be swaged onto both ends of the bidirectional self-retaining sutures, or the bidirectional self-retaining sutures may be used without needles.

Needles are generally only swaged onto one end of the unidirectional self-retaining sutures (although they may be swaged onto both ends). The other end of a unidirectional self-retaining suture is usually configured into a closed loop to facilitate the initial fixation of the self-retaining suture. In general, it is preferable to use less traumatic needles in terms of tip design and diameter in order to improve the holding of the self-retaining suture in tissues. In an embodiment, the ratio of the needle diameter to the suture fiber diameter is less than 3, more preferably less than 2, and even more preferably less than 1.5.

The self-retaining sutures may also be incorporated as components of medical devices. For example, the self-retaining sutures may be incorporated into devices that after implantation need to be fixed in place, and wherein the self-retaining suture can be secured in soft tissue to fix the device in place. In one embodiment, the self-retaining sutures may be incorporated into surgical meshes and nonwoven constructs. Such meshes may be used in applications including hernia repair, pelvic floor reconstruction, tendon and ligament repair, breast reconstruction, plastic surgery including mastopexy, breast augmentation, face-lift, forehead lift, neck lift, brow lift, eyelid lift, and cosmetic repairs. In another embodiment, the self-retaining sutures may be incorporated inside another device or structural component of a device, for example, to provide reinforcement to the device. For example, one or more self-retaining sutures may be inserted inside a braided tube or covered with a sheath of multifilament. In a preferred embodiment, the retainers anchor the suture in the device. The retainers may or may not protrude from the sheath of the device.

E. Sterilization of High Tensile Strength Self-Retaining Sutures

In a preferred embodiment, the high tensile strength self-retaining sutures (or structures comprising these sutures) may be sterilized using ethylene oxide gas, and even more preferably using an ethylene oxide cold cycle. In another preferred embodiment, the high tensile strength sutures (or structures comprising these sutures) may be sterilized with electron-beam irradiation or gamma-irradiation. In another embodiment, the high strength self-retaining sutures may be sterilized using alcohol.

IV. Methods of Implanting High Strength Self-Retaining Sutures and Applications

The self-retaining sutures may be implanted in straight lines. However, it is generally preferable, although not always, to implant the self-retaining sutures in a configuration that is not a straight line. It is believed that the self-retaining sutures anchor better in tissue when the self-retaining sutures are placed in winding, twisting, or meandering patterns so that the retainers encounter more collagen to ensnare. In contrast, if the self-retaining suture is placed in a straight line, there is a risk that a loosened tunnel of tissue may form around the suture if the suture begins to pull out. Greater holding strength may therefore be achieved if the self-retaining suture is placed, for example, with a "J" stitch rather than a straight stitch. Similarly, the self-retaining suture may be placed in other configurations, such as "U", "C", "S" or "M" patterns, to provide greater holding strength.

The high strength absorbable self-retaining sutures may be used in procedures where temporary support is required. For example, the sutures may be used in certain repair and remodeling procedures. The self-retaining sutures may be used in the approximation of wounds, including deep wounds, and may be used to reduce the formation of wide scars and wound hernias. This may be possible, for example, in cases where a self-retaining suture can more evenly spread the tension in a wound when compared to the use of a conventional smooth knotted suture.

In a particularly preferred embodiment, the self-retaining sutures are used in plastic surgery procedures, and even more preferably in lift procedures. The sutures may be used, for example, to approximate tissues in the face, neck and breast, and to elevate these tissues. For example, the self-retaining sutures may be used to elevate a ptotic breast in mastopexy procedures, either using just sutures or in combination with other materials, such as a surgical mesh. The sutures may also be anchored to the superior pectoral fascia, and used, for example to elevate the nipple during augmentation, capsulectomy, or lipoplasty reductions. In the face and neck, the self-retaining sutures may be used in face-lift, forehead lift, neck lift, brow lift, and eyelid lift procedures. For example, the self-retaining sutures can be used in lateral canthopexy (lower eyelid suspension surgery) to fix eyelids that droop or sag, or extended from the scalp into the brow, nasolabial folds, jowls, or central neck. During lift procedures, the self-retaining sutures can be used to displace redundant tissue, for example, up into the hairline.

In other preferred embodiments, the self-retaining sutures may be used in: obstetrics and gynecological procedures, such as myomectomy, hysterectomy, sacrocolpopexy, and hemostasis, anastomosis, abdominal closure, laparoscopic procedures, partial nephrectomy, and tendon and ligament repair.

In still other embodiments, the sutures may be incorporated as part of a device. Exemplary devices include, but are not limited to braided suture, hybrid suture of monofilament and multifilament fibers, braid, ligature, knitted or woven mesh, knitted tube, monofilament mesh, multifilament mesh, patch, wound healing device, bandage, wound dressing, burn dressing, ulcer dressing, skin substitute, hemostat, tracheal reconstruction device, organ salvage device, dural substitute, dural patch, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, stent, including coronary, cardiovascular, peripheral, ureteric, urethral, urology, gastroenterology, nasal, ocular, or neurology stents and stent coatings, stent graft, cardiovascular patch, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, embolization device, anastomosis device, cell seeded device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision.

EXAMPLES

The present invention will be further understood by reference to the following non-limiting examples.

Example 1: Extrusion of High Strength P4HB Monofilament

Bulk P4HB resin in pellet form was dried to under 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and an eight-hole spinneret assembly. Processing profile ranges from 40° C. to 260° C. for temperatures, and 400 psi to 2000 psi for pressures, were used. The molten filaments were water quenched and conveyed into a three-stage orientation, before winding of the monofilaments on spools. In the three-stage orientation, the filaments were stretched 7×. Test values for extruded and oriented high strength P4HB monofilament fiber are shown in Table 4.

TABLE 4

Mechanical Test Data for High Strength P4HB Monofilament Fiber

| Fiber USP Size | Diameter, μm | Tensile Strength, Kgf | Break Elongation | Young's Modulus, GPa |
|---|---|---|---|---|
| 3/0* | 286 | 6.9 | 25% | 1.8 |
| 2 | 584 | 26.1 | 28% | 1.3 |

*example is oversized

Comparative Example 1: Extrusion of Medium Strength P4HB Monofilament

Bulk P4HB resin in pellet form was dried to under 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and an eight-hole spinneret assembly. Processing profile ranges from 40° C. to 260° C. for temperatures, and 400 psi to 2000 psi for pressures, were used. The molten filaments were water quenched and conveyed into a three-stage orientation, with inline relaxation, before winding of the monofilaments on spools. In the three-stage orientation, the filaments were stretched 7× then relaxed to 6.5×. Test values for extruded and oriented medium strength P4HB monofilament fiber are shown in Table 5.

TABLE 5

Mechanical Test Data for Medium Strength P4HB Monofilament Fiber

| Fiber USP Size | Diameter, μm | Tensile Strength, Kgf | Break Elongation | Young's Modulus, GPa |
|---|---|---|---|---|
| 0* | 440 | 10.9 | 54% | 0.75 |
| 2/0* | 352 | 6.4 | 57% | 0.72 |
| 3/0* | 281 | 4.4 | 57% | 0.79 |

*example is oversized

Example 2: Preparation of an Oversized Size 3/0 High Strength P4HB Self-Retaining Suture Meeting USP for Knot Strength A high strength oversized size 3/0 poly-4-hydroxybutyrate monofilament, with a diameter of 286 μm, tensile strength of 6.9 Kgf, elongation to break of 25%, and a Young's Modulus of 1.8 GPa, was mechanically cut to form a self-retaining suture. The monofilament was cut using an angle of 21.8 degrees measured relative to the longitudinal axis of the monofilament fiber (as shown in FIG. 1), and the depth of the cut (measured perpendicular to the longitudinal axis of the monofilament fiber) was 120 μm. The length of the cut was 300 μm. The cuts were spaced at a distance of 300 μm apart with each successive cut offset from the prior cut at an angle of 120 degrees around the circumference of the fiber. The density of cuts was 33.3 per cm of monofilament length. After cutting, the self-retaining monofilament fiber had a tensile strength of 2.5 Kgf, elongation to break of 22%, and a Young's Modulus of 1.8 GPa. Notably, the tensile strength of the self-retaining suture was 41% higher than the minimum USP knot strength of 1.77 Kgf required for a size 3/0 suture.

Comparative Example 2: Preparation of an Oversized Size 3/0 Medium Strength P4HB Self-Retaining Suture not Meeting USP for Knot Strength A medium strength oversized size 3/0 poly-4-hydroxybutyrate monofilament, with a diameter of 281 μm, tensile strength of 4.4 Kgf, elongation to break of 57%, and a Young's Modulus of 0.79 GPa, was mechanically cut to form a self-retaining suture. The monofilament was cut as listed in the above example 2. After placement of the retainers, the self-retaining monofilament suture had a tensile strength of 1.6 Kgf, elongation to break of 28%, and a Young's Modulus of 0.79 GPa. Notably, the tensile strength of the barbed suture was 9.6% lower than the minimum USP knot strength of 1.77 Kgf required for a size 3/0 suture.

Example 3: Preparation of a Size 2 High Strength P4HB Self-Retaining Suture Meeting USP for Knot Strength A high strength size 2 poly-4-hydroxybutyrate monofilament, with a diameter of 584 µm, tensile strength of 26.1 Kgf, elongation to break of 28%, and a Young's Modulus of 1.3 GPa, was mechanically cut to form a self-retaining suture. The monofilament was cut using an angle of 21 degrees measured relative to the longitudinal axis of the monofilament fiber (see FIG. 1), and the depth of the cut (measured perpendicular to the longitudinal axis of the monofilament fiber) was 230 µm. The length of the cut was 600 µm. The cuts were spaced at a distance of 600 µm apart with each successive cut offset from the prior cut at an angle of 120 degrees around the circumference of the fiber. The density of cuts was 16.6 per cm of monofilament. After placement of the retainers, the self-retaining monofilament suture had a tensile strength of 7.7 Kgf, elongation to break of 27%, and a Young's Modulus of 1.3 GPa. Notably, the tensile strength of the self-retaining suture was 21% higher than the minimum USP knot strength of 6.35 Kgf required for a size 2 suture.

Comparative Example 4: Preparation of an Oversized Size 0 Medium Strength P4HB Self-Retaining Suture not Meeting USP for Knot Strength A medium strength oversized size 0 poly-4-hydroxybutyrate monofilament, with a diameter of 440 µm, tensile strength of 10.9 Kgf, elongation to break of 54%, and a Young's Modulus of 0.75 GPa, was mechanically cut to form a self-retaining suture. The monofilament was cut using an angle of 23.7 degrees measured relative to the longitudinal axis of the monofilament fiber (see FIG. 1), and the depth of the cut (measured perpendicular to the longitudinal axis of the monofilament fiber) was 176 µm. The length of the cut was 400 µm. The cuts were spaced at a distance of 500 µm apart with each successive cut offset from the prior cut at an angle of 120 degrees around the circumference of the fiber. The density of cuts was 20 per cm of monofilament. After placement of the retainers, the self-retaining monofilament suture had a tensile strength of 3.2 Kgf, elongation to break of 31%, and a Young's Modulus of 0.64 GPa. Notably, the tensile strength of the self-retaining suture was 17.9% lower than the minimum USP knot strength of 3.9 Kgf required for a size 0 suture.

Comparative Example 5: Preparation of an Oversized Size 2/0 Medium Strength P4HB Self-Retaining Suture not Meeting USP for Knot Strength A medium strength oversized size 2/0 poly-4-hydroxybutyrate monofilament, with a diameter of 352 µm, tensile strength of 6.4 Kgf, elongation to break of 57%, and a Young's Modulus of 0.72 GPa, was mechanically cut to form a self-retaining suture. The monofilament was cut using an angle of 22.4 degrees measured relative to the longitudinal axis of the monofilament fiber, and the depth of the cut (measured perpendicular to the longitudinal axis of the monofilament fiber) was 140 µm. The length of the cut was 340 µm. The cuts were spaced at a distance of 350 µm apart with each successive cut offset from the prior cut at an angle of 120 degrees around the circumference of the fiber. The density of cuts was 28 per cm of monofilament. After placement of the retainers, the self-retaining monofilament fiber had a tensile strength of 2.4 Kgf, elongation to break of 31%, and a Young's Modulus of 0.79 GPa. Notably, the tensile strength of the self-retaining suture was 10% lower than the minimum USP knot strength of 2.68 Kgf required for a size 2/0 suture.

Modifications and variations of the self-retaining monofilament sutures and methods of making and using described herein are intended to come within the scope of the appended claims. All references cited herein are specifically incorporated by reference.

We claim:

1. An absorbable self-retaining suture made from a monofilament fiber, wherein the monofilament fiber comprises a sheath-core structure, wherein the core structure comprises the same polymer as the sheath, and the core and sheath are oriented, wherein the fiber has been stretched at least 6 times its original length without subsequent relaxation of the fiber, wherein the sheath and the core have indentation hardness, and the indentation hardness of the sheath is higher than the indentation hardness of the core, and wherein the self-retaining suture minimum straight pull tensile strength is selected from the group consisting of
   (i) 0.25 Kgf when the average suture diameter is between 0.070 and 0.099 mm;
   (ii) 0.68 Kgf when the average suture diameter is between 0.10 and 0.149 mm;
   (iii) 0.95 Kgf when the average suture diameter is between 0.15 and 0.199 mm;
   (iv) 1.77 Kgf when the average suture diameter is between 0.20 and 0.249 mm;
   (v) 2.68 Kgf when the average suture diameter is between 0.30 and 0.339 mm;
   (vi) 3.90 Kgf when the average suture diameter is between 0.35 and 0.399 mm;
   (vii) 5.08 Kgf when the average suture diameter is between 0.40 and 0.499 mm;
   (viii) 6.35 Kgf when the average suture diameter is between 0.50 and 0.599 mm; and
   (ix) 7.29 Kgf when the average suture diameter is between 0.60 and 0.699 mm.

2. The absorbable self-retaining suture of claim 1, wherein the minimum straight pull tensile strength of the self-retaining suture is selected from the group consisting of:
   (i) 0.25 Kgf when the average suture diameter is between 0.070 and 0.149 mm;
   (ii) 0.68 Kgf when the average suture diameter is between 0.10 and 0.199 mm;
   (iii) 0.95 Kgf when the average suture diameter is between 0.15 and 0.249 mm;
   (iv) 1.77 Kgf when the average suture diameter is between 0.20 and 0.349 mm;
   (v) 2.68 Kgf when the average suture diameter is between 0.30 and 0.439 mm;
   (vi) 3.90 Kgf when the average suture diameter is between 0.35 and 0.499 mm;

(vii) 5.08 Kgf when the average suture diameter is between 0.40 and 0.599 mm;
(viii) 6.35 Kgf when the average suture diameter is between 0.50 and 0.699 mm; and
(ix) 7.29 Kgf when the average suture diameter is between 0.60 and 0.799 mm.

3. The self-retaining sutures of claim 1 made from a monofilament fiber having a characteristic selected from the group consisting of: (a) a monofilament fiber that has been stretched at least 6 times its original length without subsequent relaxation of the fiber; (b) a straight pull tensile strength that is at least two times that of the self-retaining suture; and (c) a monofilament fiber that has been cut through up to 40% of its diameter.

4. The monofilament fiber of claim 3 wherein the fiber has a Young's modulus greater than 860 MPa.

5. The self-retaining sutures of claim 3 wherein the sheath comprises a surface, wherein the surface of the sheath of the self-retaining suture has an average indentation hardness of at least 0.07 GPa.

6. The self-retaining sutures of claim 3 wherein the core of the self-retaining suture has an indentation hardness of less than 0.07 GPa.

7. The self-retaining sutures of claim 1 comprising a monofilament fiber and retainers, wherein the retainers are cut, stamped, machined, molded or welded.

8. The self-retaining sutures of claim 1 wherein the monofilament has cut at an angle of less than 60 degrees, wherein the angle is measured relative to the longitudinal axis of the monofilament fiber.

9. The self-retaining sutures of claim 8 wherein the cuts are spaced at a distance of at least half the diameter of the monofilament fiber, offset from one another, placed in a helical pattern, overlapping, ordered, staggered, random unidirectional bidirectional or combinations thereof along the length of the self-retaining suture.

10. The self-retaining sutures of claim 8 wherein the length of the cut to make the retainers is between one-quarter to twice the diameter of the monofilament fiber.

11. The self-retaining sutures of claim 1 wherein the sutures further comprise one or more needles, a looped end, or a needle on one end and a loop at the other end.

12. The self-retaining sutures of claim 1 wherein the sutures contain less than 20 endotoxin units (EU) per suture.

13. The self-retaining sutures of claim 1 wherein the sutures have been sterilized by ethylene oxide, electron beam irradiation, or gamma-irradiation.

14. The self-retaining sutures of claim 1 further comprising a coating selected from the group consisting of a wax, natural polymer, synthetic polymer, resorbable polymer or combinations thereof, or an additive selected from the group consisting of plasticizers, nucleants, compatibilizers, porogens, radiolabelled substances, imaging agents, radiopaque markers, contrast agents, dyes, and bioactive agents.

15. The self-retaining sutures of claim 1 wherein the suture comprises a blend of an absorbable polymer with a natural polymer, synthetic polymer, or second absorbable polymer.

16. The self-retaining sutures of claim 15 wherein the second absorbable polymer comprises a monomer selected from the group consisting of glycolic acid, lactic acid, 1,4-dioxanone, trimethylene carbonate or ε-caprolactone.

17. The self-retaining sutures of claim 1 wherein (a) the core structure and the sheath structure comprise suture comprises poly-4-hydroxybutyrate homopolymer, or (b) the core structure and the sheath structure comprise a copolymer of poly-4-hydroxybutyrate.

18. The self-retaining suture of claim 17 wherein the weight average molecular weight of the poly-4-hydroxybutyrate or copolymer thereof is between 50 kD and 1,200 kD.

19. The self-retaining sutures of claim 1 wherein the suture is a component of a device selected from the group consisting of a braided suture, hybrid suture of monofilament and multifilament fibers, braid, ligature, knitted or woven mesh, knitted tube, monofilament mesh, multifilament mesh, patch, wound healing device, bandage, wound dressing, burn dressing, ulcer dressing, skin substitute, hemostat, tracheal reconstruction device, organ salvage device, dural substitute, dural patch, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, stent, including coronary, cardiovascular, peripheral, ureteric, urethral, urology, gastroenterology, nasal, ocular, or neurology stents and stent coatings, stent graft, cardiovascular patch, vascular closure device, intracardiac septal defect repair device, pericardial patch, vein valve, heart valve, vascular graft, myocardial regeneration device, periodontal mesh, guided tissue regeneration membrane for periodontal tissue, embolization device, anastomosis device, cell seeded device, controlled release device, drug delivery device, plastic surgery device, breast lift device, mastopexy device, breast reconstruction device, breast augmentation device, breast reduction, reshaping or reorienting device, devices for breast reconstruction following mastectomy with or without breast implants, facial reconstructive device, forehead lift device, brow lift device, eyelid lift device, face lift device, rhytidectomy device, thread lift device to lift and support sagging areas of the face, brow and neck, rhinoplasty device, device for malar augmentation, otoplasty device, neck lift device, mentoplasty device, cosmetic repair device, and device for facial scar revision.

20. A method for preparing the self-retaining sutures of claim 1 comprising:
(a) spinning and orienting a monofilament fiber of poly-4-hydroxybutyrate or copolymer thereof wherein the average surface indentation hardness is at least 0.07 GPa; and
(b) inserting retainers in the monofilament fiber to form self-retaining sutures, wherein the straight pull tensile strength of the self-retaining suture is equal to or greater than the average minimum knot-pull tensile strength standard set by the USP for a suture of corresponding size.

21. The method of claim 20 wherein the oriented monofilament fiber has a Young's modulus greater than 860 MPa.

22. The method of claim 20 wherein the self-retaining suture comprises one or more of the following: (i) a distance between any two retainers of 0-25 mm, (ii) a length of any retainer between 0.01-10 mm, (iii) a retainer placed at an angle between 5 and 60 degrees, wherein the angle is measured relative to the longitudinal axis of the monofilament fiber, (iv) a retainer placed with a depth in the monofilament fiber of between 1 and 350 µm, (v) a retainer placed with a depth in the monofilament fiber of up to 40% of the diameter of the monofilament fiber (vi) retainers are positioned in ordered, random, spiral, staggered, or overlapping configurations and (vii) the self-retaining suture further comprises a needle at one end or needles at both ends of the suture fiber.

23. The method of making the self-retaining sutures of claim 20 comprising:
   (i) drying bulk P4HB resin in pellet form until it has a water content of less than 300 ppm using a rotary vane vacuum pump system,
   (ii) transferring the dried pellets to the feed hopper of the extruder fitted with a dry nitrogen purge to keep the pellets dry,
   (iii) gravity feeding the P4HB pellets into a chilled feeder section, introducing the pellets into the extruder barrel, feeding the heated and softened resin into a heated metering pump (melt pump), and from the metering pump feeding the resin into a heated block and an eight-hole spinneret assembly, using a processing profile of 40° C. to 260° C. for temperatures, and 400 psi to 2,000 psi for pressures,
   (iv) water quenching the molten P4HB monofilaments, and
   (v) conveying the quenched filaments into a multi-stage orientation line, and stretching of at least 6×, before winding the high strength P4HB monofilament fiber on spools.

24. A method of using the self-retaining suture of claim 1 comprising implanting the suture in the body.

25. The method of claim 24 wherein the self-retaining suture is used in obstetrics and gynecological surgery, myomectomy, hysterectomy, sacrolpopexy, cesarean delivery, orthopedic surgery, ligament and tendon repair, wound closure, reduction of wide scar reduction, wound hernias, plastic surgery, lift procedures, mastopexy, breast reconstruction, breast augmentation, breast lift, elevation of the nipple, face-lift, forehead lift, neck lift, brow lift, eyelid lift, lateral canthopexy, hemostasis, cardiovascular surgery, anastomosis, abdominal closure, laparoscopic procedures, and partial nephrectomy.

26. A monofilament fiber of poly-4-hydroxybutyrate or copolymer thereof comprising a sheath-core structure, wherein the monofilament has a Young's modulus greater than 860 MPa, wherein (a) the core structure and the sheath structure comprise poly-4-hydroxybutyrate homopolymer, or (b) the core structure and the sheath structure comprise or a copolymer of poly-4-hydroxybutyrate, wherein the fiber has been stretched at least 6 times its original length without subsequent relaxation of the fiber, wherein the sheath and the core have indentation hardness, and the indentation hardness of the sheath is higher than the indentation hardness of the core.

27. The monofilament fiber of claim 26 wherein the monofilament fiber comprises a surface, wherein the surface of the monofilament fiber has an average indentation hardness of at least 0.07 GPa.

28. The monofilament fiber of claim 26, wherein the core of the self-retaining suture has an indentation hardness of less than 0.07 GPa.

29. The monofilament fiber of claim 26 wherein the fiber has been stretched at least 6.6 times its original length without subsequent relaxation of the fiber.

30. A medical device comprising the monofilament fiber of claim 24 wherein the device is selected from the group consisting of
   a suture, braided suture, hybrid suture of monofilament and multifilament fibers, braid, ligature, knitted or woven mesh, knitted tube, monofilament mesh, multifilament mesh, patch, wound healing device, bandage, wound dressing, burn dressing, ulcer dressing, skin substitute, hemostat, tracheal reconstruction device, organ salvage device, dural substitute, dural patch, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, stent, including coronary, cardiovascular, peripheral, ureteric, urethral, urology, gastroenterology, nasal, ocular, or neurology stents and stent coatings, stent graft, cardiovascular patch, vascular closure device, intracardiac septal defect repair device, left atrial appendage (LAA) closure device, pericardial patch, vein valve, heart valve, vascular graft, myocardial regeneration device, periodontal mesh, guided tissue regeneration membrane for periodontal tissue, embolization device, anastomosis device, cell seeded device, controlled release device, drug delivery device, plastic surgery device, breast lift device, mastopexy device, breast reconstruction device, breast augmentation device, breast reduction, reshaping or reorienting device, devices for breast reconstruction following mastectomy with or without breast implants, facial reconstructive device, forehead lift device, brow lift device, eyelid lift device, face lift device, rhytidectomy device, thread lift device to lift and support sagging areas of the face, brow and neck, rhinoplasty device, device for malar augmentation, otoplasty device, neck lift device, mentoplasty device, cosmetic repair device, and device for facial scar revision.

* * * * *

UNITED STATES PATENT AND TRADEMARK OFFICE
CERTIFICATE OF CORRECTION

PATENT NO. : 10,500,303 B2
APPLICATION NO. : 14/821145
DATED : December 10, 2019
INVENTOR(S) : Rizk et al.

Page 1 of 1

It is certified that error appears in the above-identified patent and that said Letters Patent is hereby corrected as shown below:

In the Specification

Column 4, Line 28, replace "(0.1535 GPaand" with --(0.1535 GPa and--.
Column 15, Line 22, replace "preferably applied so the" with --preferably applied to the--.
Column 15, Line 43, replace "tetrahydrofura" with --tetrahydrofuran--.
Column 15, Line 56, replace "nature materials" with --natural materials--.

In the Claims

Claim 8, Column 25, Line 28, replace "has cut" with --has been cut--.
Claim 9, Column 25, Line 35, replace "unidirectional bidirectional" with --unidirectional, bidirectional--.
Claim 17, Column 25, Lines 64-65, replace "and the sheath structure comprise suture comprises" with --and the sheath structure comprise--.
Claim 26, Column 27, Line 49, replace "and the sheath structure comprise or" with --and the sheath structure comprise--.

Signed and Sealed this
Twenty-eighth Day of July, 2020

Andrei Iancu
*Director of the United States Patent and Trademark Office*